US006803362B2

(12) United States Patent
Carruthers et al.

(10) Patent No.: US 6,803,362 B2
(45) Date of Patent: Oct. 12, 2004

(54) HETEROCYCLIC COMPOUNDS

(75) Inventors: Nicholas I. Carruthers, Poway, CA (US); Wenying Chai, San Diego, CA (US); Curt A. Dvorak, San Diego, CA (US); James P. Edwards, San Diego, CA (US); Cheryl A. Grice, Carlsbad, CA (US); Jill A. Jablonowski, San Diego, CA (US); Lars Karlsson, La Jolla, CA (US); Haripada Khatuya, San Diego, CA (US); Jennifer D. Kreisberg, Del Mar, CA (US); Annette K. Kwok, San Diego, CA (US); Timothy W. Lovenberg, San Diego, CA (US); Kiev S. Ly, San Diego, CA (US); Barbara Pio, San Diego, CA (US); Chandravadan R. Shah, San Diego, CA (US); Siguan Sun, San Diego, CA (US); Robin L. Thurmond, San Diego, CA (US); Jianmei Wei, San Diego, CA (US); Wei Xiao, San Diego, CA (US)

(73) Assignee: Ortho-McNeil Pharmaceutical inc., Raritan, NJ (US)

( * ) Notice: Subject to any disclaimer, the term of this patent is extended or adjusted under 35 U.S.C. 154(b) by 111 days.

(21) Appl. No.: 10/094,357

(22) Filed: Mar. 8, 2002

(65) Prior Publication Data

US 2003/0207893 A1 Nov. 6, 2003

Related U.S. Application Data

(60) Provisional application No. 60/274,900, filed on Mar. 9, 2001, and provisional application No. 60/343,259, filed on Dec. 21, 2001.

(51) Int. Cl.$^7$ ...................... A61K 31/33; A61K 31/495; C07D 241/00; C07D 209/04; C07D 403/00

(52) U.S. Cl. .................. 514/183; 514/254.09; 544/358; 544/372; 548/452; 548/469; 548/465; 548/517; 548/518

(58) Field of Search ................................ 514/183, 254, 514/9; 544/358, 372; 548/452, 469, 465, 517, 518

(56) References Cited

U.S. PATENT DOCUMENTS

| | | | |
|---|---|---|---|
| 4,115,569 A | | 9/1978 | Weber et al. |
| 4,374,990 A | | 2/1983 | Weber et al. |
| 5,563,142 A | | 10/1996 | Palmer et al. |
| 5,614,523 A | * | 3/1997 | Audia et al. ........... 514/254.08 |
| 5,795,894 A | * | 8/1998 | Shue et al. ............ 514/254.08 |
| 5,814,644 A | | 9/1998 | Kulagowski et al. |
| 5,891,902 A | | 4/1999 | Machii et al. |

FOREIGN PATENT DOCUMENTS

| | | |
|---|---|---|
| DE | 2157424 A | 5/1973 |
| DE | 4307883 A1 | 9/1993 |
| EP | 0318235 A2 | 5/1989 |
| EP | 0324431 A1 | 7/1989 |
| EP | 0548798 A1 | 6/1993 |
| EP | 0624575 A1 | 11/1994 |
| EP | 0655440 A2 | 5/1995 |
| EP | 0978512 A1 | 2/2000 |
| JP | 01132579 A2 | 5/1989 |
| JP | 5025131 A | 2/1993 |
| JP | 05025131 * | 2/1993 |
| JP | 9124631 A | 5/1997 |
| SU | 10740940 A1 | 4/1992 |
| WO | WO 91/09849 A1 | 7/1991 |
| WO | WO 94/09781 | 5/1994 |
| WO | WO 97/03965 | 2/1997 |
| WO | WO 98/01443 | 1/1998 |
| WO | WO 99/05121 | 2/1999 |
| WO | WO 99/09025 A2 | 2/1999 |
| WO | 9909025 * | 2/1999 |
| WO | WO 01/64676 A2 | 9/2001 |
| WO | WO 01/74774 A1 | 10/2001 |

OTHER PUBLICATIONS

Chemical Abstracts, vol. 78, No. 15, Apr. 16, 1973 Columbus, Ohio, Burov, Yu. V. et al.; "Derivatives of benzofuran–2–carboxylic acids and their action on the central nervous system." XP002210361.

Chemical Abstracts, vol. 130, No. 4, Jan. 25, 1999, Columbus, Ohio, Chang, Mayland et al., "Absorption, distribution, metabolism, and excretion of atevirdine in the rat." XP002210368.

Siavosh Mahboobi et al., "Synthetic 2–aroylindoie derivatives as a new class of potent tubulin–inhibitory, antimitoic agents" Journal of Medicinal Chemistry, vol. 44, No. 26, 2001 pp. 4535–4653 XP002210359.

Chemical Abstracts, vol. 127, No. 3, Jul. 21, 1997 Columbus, Ohio, Takashima, Junko: "Preparation of benzofuran derivatives as antihypertensive agents" XP002210363.

Chemical Abstracts, vol. 121, No. 19, Nov. 7, 1994, Columbus, Ohio, Zawadowski, Teddor et al., "Synthesis of piperazinamides of benzofuran–2–and 3–carboxylic acids," XP002210364 & Abstract ACTA Pol. Pharm., vol. 50, No. 6 1993 pp. 457–459 & Database Caplus Online Chemical Abstract Service, Columbus, Ohio XP002210369.

Chemical Abstracts, vol. 119, No. 3, Jul. 19, 1993 Columbus, Ohio, Shibayama, Katsuhiro et al., "Preparation of piperazine or piperidine group–containing indoles and their use as anti–inflammatory, antiallergy, and anti–PAF agents." XP002210365 & JP 09325131 Toray Industries Dec. 16, 1997 & Database Caplus Online Chemical Abstract Service, Columbus, Ohio, XP002210370.

Chemical Abstracts, vol. 111, No. 19, Nov. 6, 1989, Columbus, Ohio, Komoto, Teruo et al., "Preparation of (indolylcarbonyl) piperazines as a platelet aggregation inhibitors." XP002210366 & JP 89132579 S.S. Pharmaceutical Co., Ltd. May 25, 1989 & Database Caplus Online Chemical Abstracts Service, Columbus, Ohio XP002210371.

(List continued on next page.)

*Primary Examiner*—Richard L. Raymond
*Assistant Examiner*—Sudhaker B. Patel

(57) ABSTRACT

Heterocyclic compounds and methods of making them and using them.

37 Claims, No Drawings

OTHER PUBLICATIONS

PCT Search Report for PCT/US 02/07 168 dated Aug. 20, 2002.

Agarawal, A. et al. A New Synthesis of the Potent 5–HT1 Receptor Ligand, 5–Carboxyamidotryptamine (5–CT). Synth. Commun. (1993) 23(8):1101–1110.

Alvarez, E.F. et al., Psychotropes Potentials, III. Prépparation des [(Hydroxy–5 ou Benzyloxy–5 Indolyl)–2 carbonyl]–1, alkyl–2 hydrazines of Etude de Leur Activité Inhibitrice de la Monoamine Oxydase, Bull. Soc. Chim. Fr. (1969) (6):1932–1940.

Ambekar, S.Y. Recent Developments in the Fischer Indole Synthesis. Current Science (1983) 52(12):578–582.

Betrabet, A.M. et al., Synthesis & Pharmacology of 5–Methoxyindole–2–carboxyamides & Their 3–Formyl Derivatives. Indian J. Chem. (1970) 8:704–706.

Bhandari, K. et al. Agents Acting on CNS: Part XXXIII—Synthesis of 1,2,3,4,6,7,8,12c–Octahydropyrazino[2',1':2,1] pyrido[4,3–b]indole & Some 2–Substituted Aminoalkylindoles. Indian J. Chem. (1979) 17B:246–249.

DE Costa, B.R. et al. Synthesis and Evaluation of Conformationally Restricted N–[2–(3,4–Dichlorphenyl)ethyl]–N–methyl–2–(1–pyrrolidinyl)ethylamines at sigma Receptors. 2. Piperazines, Bicyclic Amines, Bridged Bicyclic Amines, and Miscellaneous Compounds. J. Med. Chem. (1993) 36:2311–2320.

Dubey, R. et al. Mass Spectral Studies of 2,5–Disubstituted Benzimidazoles, Indian J. Chem. (1987) 26B:395–397.

El–Kholy, I. E.–S. et al. Reaction of Some Coumarin and 4,6–Diaryl–2H–pyran Derivatives with Secondary Amines. J. Heterocyclic Chem. (1981) 18:105–110.

Font, M. et al. Indoles and Pyridazino[4,5–b]indoles as Non–Nucleosis Analog Inhibitors of HIV–1 Reverse Transcriptase. Eur. J. Med. Chem. (1995) 30:963–971.

Garcia, F. et al. The Synthesis of Thienopyrroles. Synthesis (1985) 143–156.

Hemetsberger, H. et al. Enazides, III: Thermolysis of alpha–Azido–cinnamates. Synthesis of Indol Carboxylates. Monatsh. Chem. (1970) 101(1):161–165.

Hemetsberger, H.; Knittel, D. Enazides, IV: Synthesis and Thermolysis of alpha–Azidoacrylates. Monatsh. Chem. (1972) 103(1):194–204.

Hughes, D.L. Progress in the Fischer Indole Reaction. A Review. Org. Prep. Proced. Int. (1993) 25(6):607–632.

Ketcha, D.M. Five–Membered Ring Systems: Pyrroles and Benzo Derivatives. Prog. Heterocycl. Chem. (1999) 11:124–143.

King, F.D. et al. 3–(2–Carboxyindol–3–yl)propionic Acid Derivatives: Antagonists of the Strychnina–Insensitive Glycine Receptor Associates with the N–Methyl–D–aspartate Receptor Complex. J. Med. Chem. (1990) 33(11):2944–2946.

Love, B.E.; Nguyen, B.T. A General Synthesis of 1–(Dialkylaminomethyl)Indoles. Synlett (1998):1123–1125.

Martinez, S.J.; Joule, J.A. The Synthesis of 2,3,4,6–Tetrahydro–5–hydroxy–2,6–dimethyl–1H–pyrido–[4,3–b]carbazole; Attempts to Synthesis 2,3,4,10–Tetrahydro–5–hydroxy–2–methyl–1H–pyrido[3,4–b] carbazole. J. Chem. Soc., Perkin Trans. 1 (1979) 3155–3160.

Monge, A. et al. Selective Thromboxane Synthetase Inhibitors and Antihypertensive Agents. New Derivatives of 4–Hydrazino–5H–pyridazino[4,5–b]indole, 4–Hydrazinopyridazino[4,5–a]indole, and Related Compounds, J. Med. Chem. (1987) 30:1029–1035.

Murakami, Y. et al. p–Toluenesulfonic Acid and Cation Exchange Resin in Aprotic Solvent: Valuable Catalysts for Fischer Indolization. Heterocycles (1984) 22(5):1211–1216.

Nagarathnam, D.; Johnson, M.E. A New Synthesis of 5–Bromo–DL–tryptophan. Synth. Commun. (1993) 23(14):2011–2017.

Nakamura, T. et al. Molecular Cloning and Characterization of a New Human Histamine Receptor, HH4R Biochem. Biophys. Res. Commun. (2000) 279:615–620.

Phillips, M.A. The Formation of 2–Substituted Benziminazoles. J. Chem. Soc. (1928):2393–2399.

Preston, P.N. Synthesis, Reactions, and Spectroscopic Properties of Benzimidazoles. Chem. Rev. (1974) 74(3):279–314.

Rastogi, R.; Sharma, S. Synthesis of 2–Substituted Benzofurans as Potential Anthelmintics. Indian J. Chem. (1982) 21B:485–487.

Romero, D.L. et al. Bis(heteroaryl)piperazine (BHAP) Reverse Transcriptase Inhibitors: Structure–Activity Relationships of Novel Substituted Indole Analogues and the Identification of 1–[(5–Methanbesulfonamido–1H–indol–2–yl)–carbonyl]–4–[3 –[(1–methylethyl)amino]–pyridinyl]piperazine Monomethanesulfonate (U–90152S), a Second–Generation Clinical Candidate. J. Med. Chem. (1993) 36(10):1505–1508.

Romero, D.L. et al. Discovery, Synthesis, and Bioactivity of Bis(heteroaryl)piperazines. 1. A Novel Class of Non–Nucleoside HIV–1 Reverse Transcriptase Inhibitors. J. Med. Chem. (1994) 37(7):999–1014.

Romero, D.L. et al. Targeting Delavirdine/Atevirdine Resistant HIV–1: Identification of (Alkylamino)piperidine–Containing Bis(heteroaryl)piperazines as Broad Spectrum HIV–1 Reverse Transcriptase Inhibitors. J. Med. Chem. (1996) 39(19):3769–3789.

Shafiee, A. et al. Synthesis and Local Anesthetic Activity of Benzo[b]furan Derivatives. J. Pharm. Sci. (1978) 67(1):125–127.

Sundberg, R.J.; Russell, H.F. Syntheses with N–Protected 2–Lithioindoles. J. Org. Chem. (1973) 38(19):3324–3330.

Suzuki, H. et al., Unexpected Formation of Quinolone Derivatives in Reissert Indole Synthesis. Synlett (2000) 8:1196–1199.

Tani, M. et al. Regioselective and Non–reductive C3–Debromination of Indole Nucleus. Synlett (1996) 9:931–932.

Yamada, F.; Somei, M. A Convenient Synthetic Approach to 4–Substituted Indoles. Heterocycles (1987) 26(5):1174–1176.

Arrang, J.–M. et al. Auto–inhibition of Brain Histamine Release Mediated by a Novel Class (H3) of Histamine Receptor. Nature (1983) 302:832–837.

Ash, A.S.F.; Schild, H.O. Receptors Mediating Some Actions of Histamine. Br. J. Pharmac. Chemother. (1966) 27:427–439.

Barger, G.; Dale, H.H. Chemical Structure and Sympathomimatic Action of Amines. J. Physiol. (1910) 41:19–59 Reprinted in Adventures in Physiology; Sir Henry H. Dale, Ed.; The Wellcome Trust: London, 1965; pp 67–98.

Black, J.W. et al. Definition and Antagonism of Histamine H2–Receptors. Nature (1972) 236:385–390.

Gantz, I. et al. Molecular Cloning of a Gene Encoding the Histamine H2 Receptor. Proc. Natl. Acad. Sci. USA (1991) 88:429–433.

Hill, S.J. et al. International Union of Pharmacology. XIII. Classification of Histamine Receptors, Pharmacol. Rev. (1997) 49(3):253–278.

Liu, C. et al. Cloning and Pharmacological Characterization of a Fourth Histamine Receptor (H4) Expressed in Bone Marrow. Mol. Pharmacol. (2001) 59(3):420–426.

Lovenberg, T.W. et al. Cloning and Functional Expression of the Human Histamine H3 Receptor. Mol. Pharmacol. (1999) 55(6):1101–1107.

Morse, K.L. et al. Cloning and Characterization of a Novel Human Histamine Receptor. J. Pharmacol. Exp. Ther. (2001) 296(3):1058–1066.

Nguyen, T. et al. Discovery of a Novel Member of the Histamine Receptor Family. Mol. Pharmacol. (2001) 59(3):427–433.

Oda, T. et al. Molecular Cloning and Characterization of a Novel Type of Histamine Receptor Preferentially Expressed in Leukocytes. J. Biol. Chem. (2000) 275(47):36781–36786.

Raible, D.G. et al. Pharmacologic Characterization of a Novel Histamine Receptor on Human Eosinophils. Am. J. Respir. Crit. Care Med. (1994) 149:1506–1511.

Yamashita, M. et al. Expression Cloning of a cDNA Encoding the Bovine Histamine H1 Receptor. Proc. Natl. Acad. Sci. USA (1991) 88:11515–11519.

Zhu, Y. et al. Cloning, Expression, and Pharmacological Characterization of a Novel Human Histamine Receptor, Mol. Pharmacol. (2001) 59(3):434–441.

* cited by examiner

HETEROCYCLIC COMPOUNDS

This application claims the benefit of provisional U.S. Application Sr. No. 60274900 filed on Mar. 9, 2001, and provisional U.S. Sr. No. 60343259, filed Dec. 21, 2001.

FIELD OF THE INVENTION

The invention relates to novel, pharmaceutically-active fused heterocyclic compounds and methods of using them to treat or prevent disorders and conditions mediated by the histamine $H_4$ receptor.

BACKGROUND

Histamine was first identified as a hormone (Barger et al., *J. Physiology* 41:19–59, 1910) and has since been demonstrated to play a major role in a variety of physiological processes, including the inflammatory "triple response" via $H_1$ receptors (Ash et al., *Br. J. Pharmacology* 27:427–439, 1966), gastric acid secretion via $H_2$ receptors (Black et al., *Nature* 236:385–390, 1972), and neurotransmitter release in the central nervous system via $H_3$ receptors (Arrang et al., *Nature* 302: 832–837, 1983) (for review see Hill et al., *Pharmacol. Rev.* 49: 253–278, 1997). All three histamine receptor subtypes have been demonstrated to be members of the superfamily of G-protein coupled receptors (Gantz et al., *Proc. Natl. Acad. Sci. U.S.A.* 88:429–433, 1991; Lovenberg et al., *Mol. Pharmacol.* 55:1101–1107, 1999; Yamashita et al., *Proc. Natl. Acad. Sci. U.S.A.* 88:11515–11519, 1991). There are, however, additional functions of histamine that have been reported, for which no receptor has been identified. For example, in 1994, Raible et al. demonstrated that histamine and R-α-methylhistamine could activate calcium mobilization in human eosinophils (Raible et al., *Am. J. Respir. Crit. Care Med.* 149:1506–1511, 1994). These responses were blocked by the $H_3$-receptor antagonist thioperamide. However, R-α-methylhistamine was significantly less potent than histamine which was not consistent with the involvement of known $H_3$ receptor subtypes. Therefore, Raible et al. hypothesized the existence of a novel histamine receptor on eosinophils that was non-$H_1$, -$H_2$, or -$H_3$. Most recently several groups (Oda et al., *J. Biol. Chem.* 275(47): 36781–36786, 2000; Liu et al., *Mol. Pharmacol.* 59:420–426, 2001; Nguyen et al., *Mol. Pharmacol.* 59:427–433, 2001; Zhu et al., *Mol. Pharmacol.* 59(3): 434–441, 2001; Morse et al., *J. Pharmacol. Exp. Ther.* 296(3):1058–1066, 2001) have identified and characterized a fourth histamine receptor subtype, the $H_4$ receptor. This receptor is a 390 amino-acid, seven-transmembrane G protein coupled receptor with approximately 40% homology to the histamine $H_3$ receptor. In contrast to the $H_3$ receptor, which is primarily located in the brain, the $H_4$ receptor is expressed at greater levels in neutrophils and mast cells, among other cells, as reported by Morse et al. (see above).

Events that elicit the inflammatory response include physical stimulation (including trauma), chemical stimulation, infection, and invasion by a foreign body. The inflammatory response is characterized by pain, increased temperature, redness, swelling, reduced function, or a combination of these. Many conditions, such as allergies, asthma, chronic obstructed pulmonary disease (COPD), atherosclerosis, and autoimmune diseases, including rheumatoid arthritis and lupus, are characterized by excessive or prolonged inflammation. Inhibition of leukocyte recruitment can provide significant therapeutic value. Inflammatory diseases or inflammation-mediated diseases or conditions include, but are not limited to, acute inflammation, allergic inflammation, and chronic inflammation.

Mast cell de-granulation (exocytosis) leads to an inflammatory response that may be initially characterized by a histamine-modulated wheal and flare reaction. A wide variety of immunological (e.g., allergens or antibodies) and non-immunological (e.g., chemical) stimuli may cause the activation, recruitment, and de-granulation of mast cells. Mast cell activation initiates allergic ($H_1$) inflammatory responses, which in turn cause the recruitment of other effector cells that further contribute to the inflammatory response. The histamine H2 receptors modulate gastric acid secretion, and the histamine H3 receptors affect neurotransmitter release in the central nervous system.

Examples of textbooks on the subject of inflammation include J. I. Gallin and R. Snyderman, *Inflammation: Basic Principles and Clinical Correlates*, 3rd Edition, (Lippincott Williams & Wilkins, Philadelphia, 1999); V. Stvrtinova, J. Jakubovsky and I. Hulin, "Inflammation and Fever", *Pathophysiology Principles of Diseases* (Textbook for Medical Students, Academic Press, 1995); Cecil et al., *Textbook Of Medicine*, 18th Edition (W. B. Saunders Company, 1988); and Steadmans Medical Dictionary.

A summary of the present invention follows.

SUMMARY OF THE INVENTION

The invention features a compound of formula (I) wherein:

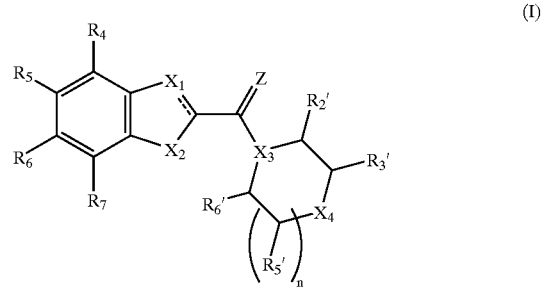

(I)

Wherein $R_1$ is $R_a$, $R_aR_b$—, $R_a$—O—$R_b$—, or $(R_c)(R_d)$N—$R_b$—, where $R_a$ is H, cyano, —(C=O)N($R_c$)($R_d$), —C(=NH)(NH$_2$), $C_{1-10}$ alkyl, $C_{3-8}$ alkenyl, $C_{3-8}$ cycloalkyl, $C_{2-5}$ heterocyclic radical, or phenyl; where $R_b$ is $C_{1-8}$ alkylene, $C_{2-8}$ alkenylene, $C_{3-8}$ cycloalkylene, bivalent $C_{3-8}$ heterocyclic radical, or phenylene; and $R_c$ and $R_d$ are each independently H, $C_{1-8}$ alkyl, $C_{2-8}$ alkenyl, $C_{3-8}$ cycloalkyl, or phenyl;

$R_2'$ is H, methyl, ethyl, NR$_p$R$_q$, —(CO)NR$_p$R$_q$, —(CO)OR$_r$, —CH$_2$NR$_p$R$_q$, or CH$_2$OR$_r$; where R$_p$, R$_q$, and R$_r$ are independently selected from $C_{1-6}$ alkyl, $C_{3-6}$ cycloalkyl, phenyl; ($C_{3-6}$ cycloalkyl)($C_{1-2}$ alkylene), benzyl or phenethyl; or R$_p$ and R$_q$ taken together with the nitrogen to which they are attached, form a 4–7 membered heterocyclic ring with 0 or 1 additional heteroatoms selected from O, S, and N;

$R_3'$ is H, methyl, ethyl, NR$_s$R$_t$, —(CO)NR$_s$R$_t$, —(CO)OR$_u$, —CH$_2$NR$_s$R$_t$, or CH$_2$OR$_u$; where R$_s$, R$_t$, and R$_u$ are independently selected from $C_{1-6}$ alkyl, $C_{3-6}$ cycloalkyl, phenyl; ($C_{3-6}$ cycloalkyl)($C_{1-2}$ alkylene), benzyl or phenethyl; or R$_s$ and R$_t$ taken together with the nitrogen to which they are attached, form a 4–7 membered heterocyclic ring with 0 or 1 additional heteroatoms selected from O, S, and N;

$R_5'$ is methyl, ethyl, or H;

$R_6'$ is methyl, ethyl, or H;

$R_7'$ is methyl, ethyl, or H;

$X_4$ is $NR_1$ or S;

$X_1$ is $CR_3$;

$R_3$ is F, Cl, Br, CHO, $R_f$, $R_fR_g$—, $R_f$—O—$R_g$—, or $(R_h)(R_i)N$—$R_g$—, where $R_f$ is H, $C_{1-6}$ alkyl, $C_{2-6}$ alkenyl, $C_{3-6}$ cycloalkyl, $C_{2-5}$ heterocyclic radical, or phenyl; where $R_g$ is $C_{1-6}$ alkylene, $C_{2-6}$ alkenylene, $C_{3-6}$ cycloalkylene, bivalent $C_{3-6}$ heterocyclic radical, or phenylene; and $R_h$ and $R_i$ are each independently H, $C_{1-6}$ alkyl, $C_{2-6}$ alkenyl, $C_{3-6}$ cycloalkyl, or phenyl;

$X_2$ is $NR_e$ or O, provided that $X_2$ is $NR_e$ where $X_1$ is N; $R_e$ is H or $C_{1-6}$ alkyl;

$X_3$ is N;

Z is =O or =S;

each of $R_4$ and $R_6$ is independently H, F, Cl, Br, I, COOH, OH, nitro, amino, cyano, $C_{1-4}$ alkoxy, or $C_{1-4}$ alkyl;

$R_5$ is H, F, Cl, Br, I, (C=O)$R_j$, OH, nitro, $NR_jR_k$, cyano, phenyl, —OCH$_2$—Ph, $C_{1-4}$ alkoxy, or $C_{1-4}$ alkyl;

$R_7$ is H, F, Cl, Br, I, (C=O)$R_m$, OH, nitro, $NR_lR_m$, cyano, phenyl, —OCH$_2$—Ph $C_{1-4}$ alkoxy, or $C_{1-4}$ alkyl;

wherein each of $R_j$, $R_k$, $R_l$, and $R_m$ is independently selected from H, $C_{1-6}$ alkyl, hydroxy, phenyl, benzyl, phenethyl, and $C_{1-6}$ alkoxy;

each of the above hydrocarbyl (including alkyl, alkoxy, phenyl, benzyl, cycloalkyl, and so on) or heterocyclic groups being independently and optionally substituted with between 1 and 3 substituents selected from $C_{1-3}$ alkyl, halo, hydroxy, amino, and $C_{1-3}$ alkoxy;

wherein n is 0, 1, or 2; where n is 2, the moiety —(CHR$_5'$)$_{n=2}$— is —(CHR$_5'$—CHR$_7'$)— where CHR$_5'$ is between CHR$_6'$ and CHR$_7'$;

provided at least one of $R_1$, $R_2'$, $R_3$, $R_4$, $R_5$, $R_6$, and $R_7$ is other than H when Z is O;

and provided, where Z is O, n=1, and each of $R_4$, $R_5$, $R_6$, $R_7$, $R_2'$, $R_3'$, $R_5'$, and $R_6'$ is H, (or at least 7, 8, or 9 of these 10 limitations apply) then (a) where $X_2$ is NH, then $R_1$ is (i) not methyl, pyridyl, phenyl, or benzyl, or (ii) is selected from the disclosed possibilities, but not $C_{1-2}$ alkyl and not a six-membered aryl or six-membered nitrogen-containing heteroaryl, or phenyl ($C_{1-2}$ alkylene) (alternatively, provided, where Z is O, n=1, and $X_2$ is NH, then at least two (or three) of $R_4$, $R_5$, $R_6$, $R_7$, $R_2'$, $R_3'$, $R_5'$, and $R_6'$ is other than H); and (b) where $X_2$ is O, then $R_1$ is not methyl;

and provided, where Z is O, $X_2$ is NH, n=1, $R_1$ is methyl, each of $R_4$, $R_6$, $R_7$, $R_2'$, $R_3'$, $R_5'$, and $R_6'$ is H (or at least 7, 8, 9, or 10 of these 11 limitations apply), then $R_5$ is (i) not methoxy, (ii) not methoxy, or ethoxy, (iii) not $C_{1-4}$ alkoxy, or (iv) not methoxy or hydroxy;

or a pharmaceutically acceptable salt, ester, or amide thereof.

According to one aspect of the invention, the invention features compounds of the following formula (Ib):

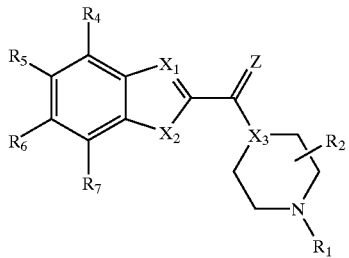

(Ib)

Wherein $R_1$ is $R_a$, $R_aR_b$—, $R_a$—O—$R_b$—, or $(R_c)(R_d)N$—$R_b$—, where $R_a$ is H, $C_{1-10}$ alkyl, $C_{3-8}$ alkenyl, $C_{3-8}$ cycloalkyl, $C_{2-5}$ heterocyclic radical, or phenyl; where $R_b$ is $C_{1-8}$ alkylene, $C_{3-8}$ alkenylene, $C_{3-8}$ cycloalkylene, bivalent $C_{3-8}$ heterocyclic radical, or phenylene; and $R_c$ and $R_d$ are each independently H, $C_{1-8}$ alkyl, $C_{3-8}$ alkenyl, $C_{3-8}$ cycloalkyl, or phenyl;

$R_2$ is ortho (like $R_2'$ in formula (I)) or meta (like $R_3'$ in formula (I)), and is methyl or H;

$X_1$ is $CR_3$;

$R_3$ is F, Cl, Br, $R_f$, $R_fR_g$—, $R_f$—O—$R_g$—, or $(R_h)(R_i)N$—$R_g$—, where $R_f$ is H, $C_{1-6}$ alkyl, $C_{2-6}$ alkenyl, $C_{3-6}$ cycloalkyl, $C_{2-5}$ heterocyclic radical, or phenyl; where $R_g$ is $C_{1-6}$ alkylene, $C_{2-6}$ alkenylene, $C_{3-6}$ cycloalkylene, bivalent $C_{3-6}$ heterocyclic radical, or phenylene; and $R_h$ and $R_i$ are each independently H, $C_{1-6}$ alkyl, $C_{2-6}$ alkenyl, $C_{3-6}$ cycloalkyl, or phenyl;

$X_2$ is $NR_e$ or O, provided that $X_2$ is $NR_e$ when $X_1$ is N; $R_e$ is H or $C_{1-6}$ alkyl;

$X_3$ is N;

Z is =O or =S;

each of $R_4$ and $R_6$ is independently H, F, Cl, Br, I, COOH, OH, nitro, amino, cyano, $C_{1-4}$ alkoxy, or $C_{1-4}$ alkyl;

$R_5$ is H, F, Cl, Br, I, (C=O)$R_j$, OH, nitro, $NR_jR_k$, cyano, —OCH$_2$—Ph, $C_{1-4}$ alkoxy, or $C_{1-4}$ alkyl;

$R_7$ is H, F, Cl, Br, I, (C=O)$R_m$, OH, nitro, $NR_lR_m$, cyano, $C_{1-4}$ alkoxy, or $C_{1-4}$ alkyl;

wherein each of $R_j$, $R_k$, $R_l$, and $R_m$ is independently selected from H, $C_{1-6}$ alkyl, hydroxy, and $C_{1-6}$ alkoxy; and each of the above hydrocarbyl or heterocyclic groups being independently and optionally substituted with between 1 and 3 substituents selected from $C_{1-3}$ alkyl, halo, hydroxy, amino, and $C_{1-3}$ alkoxy;

provided at least one of $R_1$, $R_2$, $R_3$, $R_4$, $R_5$, $R_6$, and $R_7$ is other than H when Z is =O;

or a pharmaceutically acceptable salt, ester, or amide thereof.

The invention also features methods of making and using such compounds in pharmaceutical composition, packaged drugs, and in the treatment or prevention of $H_4$-mediated diseases and conditions, particularly those wherein it is desirable to antagonize the $H_4$ receptor. For example, the expression of the $H_4$ receptor in immune cells, including some leukocytes and mast cells, establishes it as an important target for therapeutic intervention in a range of immunological and inflammatory disorders (such as allergic, chronic, or acute inflammation). Specifically $H_4$ receptor ligands are expected to be useful for the treatment or prevention of various mammalian disease states. Examples include: inflammatory disorders (such as those mediated by leukocytes or mast cells), asthma, psoriasis, rheumatoid arthritis, ulcerative colitis, Crohn's disease, inflammatory bowel disease, multiple sclerosis, allergic disorders, autoimmune disease, lymphatic disorders, atherosclerosis, and immunodeficiency disorders.

In addition, $H_4$ receptor ligands may be useful as adjuvants to chemotherapy. In the above methods of treatment, the invention also includes using compounds described in formula (I) and (Ib) without the provisos such as "provided at least one of $R_1$, $R_2$, $R_3$, $R_4$, $R_5$, $R_6$, and $R_7$ is other than H when Z is O" above in pharmaceutical compositions for treating $H_4$-mediated conditions, and in methods of treatment of $H_4$-mediated diseases. Such a compound is, for example, Example 4.

Important synthetic intermediates of the above compounds include those wherein one or more of $R_4$, $R_5$, $R_6$ and $R_7$ is Br, I, cyano, nitro, alkoxy, or —OCH$_2$Ph, which can be further modified to provide a wide range of substituents.

Other features and advantages of the invention will be apparent in the following detailed description, examples, and the appended claims.

DETAILED DESCRIPTION

The invention features compounds of formulae (I) and (Ib), methods of making them, and methods of using them in the preparation of pharmaceutical compositions for the treatment or prevention of $H_4$-mediated diseases and conditions.

A. Terms

The following terms are defined below, and by their usage throughout the disclosure.

"Alkyl" includes straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl does not include cycloalkyl.

"Alkenyl" includes straight chain and branched hydrocarbon radicals as above with at least one carbon-carbon double bond (sp$^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl does not include cycloalkenyl.

"Alkynyl" include straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and SO$_2$.

"Aryl" includes phenyl, naphthyl, biphenylyl, and so on.

"Cycloalkyl" includes cyclopropyl, cyclobutyl, cyclopentyl, cyclohexyl, cycloheptyl, cyclooctyl, and so on.

"Cycloalkenyl" includes cyclobutenyl, cyclobutadienyl, cyclopentenyl, cyclopentadienyl, cyclohexenyl, cyclohexadienyl, cyclohexatrienyl (phenyl), cycloheptenyl, and so on. "Cycloalkynyl" includes the analogous rings with one or more triple bonds.

"Heterocyclic radicals" include aromatic and nonaromatic rings having carbon atoms and at least one heteroatom (O, S, N) or heteroatom moiety (SO$_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Examples of heterocyclic radicals include thiazoylyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolidinyl, imidazolinyl, pyrazolidinyl, pyrazinyl, piperidyl, piperazinyl, indolinyl, and morpholinyl. For example, preferred heterocyclic radicals for $R_8$ include morpholinyl, piperazinyl, pyrrolidinyl, pyridyl, cyclohexylimino, cycloheptylimino, and more preferably, piperidyl.

"Halo" includes fluoro, chloro, bromo, and iodo, and preferably fluoro or chloro.

"Patient" or "subject" includes mammals such as humans and animals (dogs, cats, horses, rats, rabbits, mice, non-human primates) in need of observation, experiment, treatment or prevention in connection with the relevant disease or condition. Preferably, the patient is a human.

"Composition" includes a product comprising the specified ingredients in the specified amounts as well as any product that results directly or indirectly from combinations of the specified ingredients in the specified amounts.

Concerning the various radicals in this disclosure and in the claims, two general remarks are made. The first remark concerns valency. As with all hydrocarbon radicals (hydrocarbyl), whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. Hydrocarbyl includes alkoxy, in that the alkyl portion of an alkoxy group may be substituted. The context will indicate that the substituent is an alkylene or hydrocarbon radical with at least two hydrogen atoms removed (bivalent) or more hydrogen atoms removed (multivalent). An example of a bivalent radical linking two parts of the molecule is $R_b$ in formula (I), which can link N($R_c$)($R_d$) with the ring nitrogen atom of the rest of the molecule. Another example of a bivalent moiety is an alkylene or alkenylene.

Second, radicals or structure fragments as defined herein are understood to include substituted radicals or structure fragments. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, and 3-iodocyclopentyl), hydroxyalkyl, aminoalkyl, nitroalkyl, alkylalkyl, and so on. Preferred substitutions for $R_a$ include methyl, methoxy, trifluoromethoxy, difluoromethoxy, fluoromethoxy, fluoromethyl, difluoromethyl, perfluoromethyl (trifluoromethyl), 1-fluoroethyl, 2-fluoroethyl, ethoxy, fluoroethoxy, fluoro, chloro, and bromo, and particularly methyl, fluoromethyl, perfluoro, trifluoromethoxy, difluoromethoxy, methoxy, and fluoro.

B. Compounds

The invention features compounds of formula (I) and (Ib). Preferred compounds include those wherein: (a) $X_1$ is $CR_3$; (b) $X_3$ is N; (c) $X_2$ is N; (d) $R_1$ is H, methyl, or ethyl; (e) $X_2$ is N and $X_1$ is $CR_3$; (f) $X_2$ is O and $X_1$ is $CR_3$; (g) $X_2$ is N and Z is O; (h) $R_7$ is H or Cl; (i) $R_1$ is methyl or ethyl; $R_3'$ or $R_2'$ is, or both are, H; (k) $R_3$ is H or Cl; (l) each of $R_5$ and $R_7$ is independently selected from H, F, Cl, and Br; (m) $R_3$ is Cl; (n) at least one of $R_5$ and $R_7$ is F, Cl, Br, or methyl; (o) $R_5$, or $R_7$, or both is (are independently selected from) H, F, Cl, or Br; (p) $R_3'$ or $R_2'$ is methyl where $R_1$ is H; $R_3'$ or $R_2'$ is otherwise H; or (q) at least one of $R_5$ and $R_7$ is not H; or (r) combinations thereof.

Additional examples of preferred compounds or combinations of the above include those wherein:

(s) $X_3$ is N; $R_3$ is H or Cl; $R_5$ is F, Cl, Br, or methyl; and $R_7$ is H, F, Cl, or Br;

(t) R₃ is H or Cl; R₅ is F, Cl, Br, or methyl; and R₇ is H, F, Cl, Br, or methyl;

(u) R₂ is methyl where R₁ is H; R₂ is otherwise H; X₁ is CR₃; R₃ is H, F, or Cl; X₂ is NR_e or O, provided that X₂ is NR_e where X₁ is N; R_e is H or C₁₋₃ alkyl; Z is =O or =S; each of R₄ and R₆ is independently H, OH, C₁₋₄ alkyl, C₁₋₄ alkoxy, cyano, or amino; R₅ is H, F, Cl, Br, (C=O)R_j, OH, amino, cyano, C₁₋₄ alkoxy, or C₁₋₄ alkyl; R₇ is H, F, Cl, Br, (C=O)R_m, C₁₋₄ alkyl, C₁₋₄ alkoxy, cyano, or amino; and (v) R₃' and R₂' is methyl or H; X₁ is CR₃; R₃ is H, F, or Cl; X₂ is NR_e or O, provided that X₂ is NR_e where X₁ is N; R_e is H or C₁₋₆ alkyl; Z is =O or =S; each of R₄ and R₆ is H; R₅ is H, F, Cl, Br, methyl, ethyl, or propyl; and R₇ is H, F, Cl, Br, or C₁₋₄ alkyl.

Examples of compounds include: (4-Methyl-piperazin-1-yl)-(5-trifluoromethyl-1H-indol-2-yl)-methanone; (7-Amino-5-methyl-1H-indol-2-yl)-(4-methyl-piperazin-1-yl)-methanone; (5-Amino-7-methyl-1H-indol-2-yl)-(4-methyl-piperazin-1-yl)-methanone; (7-Amino-5-bromo-1H-indol-2-yl)-(4-methyl-piperazin-1-yl)-methanone; (5-Amino-7-bromo-1H-indol-2-yl)-(4-methyl-piperazin-1-yl)-methanone; (5-Fluoro-7-methyl-1H-indol-2-yl)-(4-methyl-piperazin-1-yl)-methanone; (7-Fluoro-5-methyl-1H-indol-2-yl)-(4-methyl-piperazin-1-yl)-methanone; (6-Bromo-5-hydroxy-1H-indol-2-yl)-(4-methyl-piperazin-1-yl)-methanone; (5-Bromo-6-hydroxy-1H-indol-2-yl)-(4-methyl-piperazin-1-yl)-methanone; (6-Bromo-7-hydroxy-1H-indol-2-yl)-(4-methyl-piperazin-1-yl)-methanone; (4-Bromo-7-hydroxy-1H-indol-2-yl)-(4-methyl-piperazin-1-yl)-methanone; (6-Bromo-7-methyl-1H-indol-2-yl)-(4-methyl-piperazin-1-yl)-methanone; and (4-Bromo-7-methyl-1H-indol-2-yl)-(4-methyl-piperazin-1-yl)-methanone.

Additional examples of compounds include: (5,7-Dichloro-1H-indol-2-yl)-piperazin-1-yl-methanone; (5,7-Difluoro-1H-indol-2-yl)-piperazin-1-yl-methanone; (5,7-Difluoro-1H-indol-2-yl)-(3-methyl-piperazin-1-yl)-methanone; (5,6-Difluoro-1H-indol-2-yl)-(4-methyl-piperazin-1-yl)-methanone; (4,6-Difluoro-1H-indol-2-yl)-(4-methyl-piperazin-1-yl)-methanone.

Further examples of compounds include: 1-(5-Chloro-1H-indole-2-carbonyl)-4-methyl-piperazine-2-carboxylic acid methyl ester; 4-(5-Chloro-1H-indole-2-carbonyl)-1-methyl-piperazine-2-carboxylic acid methyl ester; 4-(5-Chloro-1H-indole-2-carbonyl)-1-methyl-piperazine-2-carboxylic acid amide; 1-(5-Chloro-1H-indole-2-carbonyl)-4-methyl-piperazine-2-carboxylic acid amide; 4-(5-Chloro-1H-indole-2-carbonyl)-1-methyl-piperazine-2-carboxylic acid methylamide; 1-(5-Chloro-1H-indole-2-carbonyl)-4-methyl-piperazine-2-carboxylic acid methylamide; 4-(5-Chloro-1H-indole-2-carbonyl)-1-methyl-piperazine-2-carboxylic acid dimethylamide; 1-(5-Chloro-1H-indole-2-carbonyl)-4-methyl-piperazine-2-carboxylic acid dimethylamide; (5-Chloro-1H-indol-2-yl)-(3-hydroxymethyl-4-methyl-piperazin-1-yl)-methanone; (5-Chloro-1H-indol-2-yl)-(3-methoxymethyl-4-methyl-piperazin-1-yl)-methanone; (5-Chloro-1H-indol-2-yl)-(2-methoxymethyl-4-methyl-piperazin-1-yl)-methanone; (5-Chloro-1H-indol-2-yl)-(4-methyl-3-methylaminomethyl-piperazin-1-yl)-methanone; (5-Chloro-1H-indol-2-yl)-(4-methyl-2-methylaminomethyl-piperazin-1-yl)-methanone; (5-Chloro-1H-indol-2-yl)-(3-dimethylaminomethyl-4-methyl-piperazin-1-yl)-methanone; and (5-Chloro-1H-indol-2-yl)-(2-dimethylaminomethyl-4-methyl-piperazin-1-yl)-methanone.

Examples of preferred compounds include: (5-Chloro-1H-indol-2-yl)-(4-methyl-piperazin-1-yl)-methanone; (5-Fluoro-1H-indol-2-yl)-(4-methyl-piperazin-1-yl)-methanone; (5-Bromo-1H-indol-2-yl)-(4-methyl-piperazin-1-yl)-methanone; (5-Methyl-1H-indol-2-yl)-(4-methyl-piperazin-1-yl)-methanone; (5,7-Difluoro-1H-indol-2-yl)-(4-methyl-piperazin-1-yl)-methanone; (7-Chloro-1H-indol-2-yl)-(4-methyl-piperazin-1-yl)-methanone; (5,7-Dichloro-1H-indol-2-yl)-(4-methyl-piperazin-1-yl)-methanone; and (3,5-Dichloro-1H-indol-2-yl)-(4-methyl-piperazin-1-yl)-methanone. More preferred compounds in this group include (5-Chloro-1H-indol-2-yl)-(4-methyl-piperazin-1-yl)-methanone; (5-Bromo-1H-indol-2-yl)-(4-methyl-piperazin-1-yl)-methanone; (5-Methyl-1H-indol-2-yl)-(4-methyl-piperazin-1-yl)-methanone; (5,7-Difluoro-1H-indol-2-yl)-(4-methyl-piperazin-1-yl)-methanone; (5-Fluoro-1H-indol-2-yl)-(4-methyl-piperazin-1-yl)-methanone; (7-Amino-1H-indol-2-yl)-(4-methyl-piperazin-1-yl)-methanone; (7-Methyl-1H-indol-2-yl)-(4-methyl-piperazin-1-yl)-methanone; and (5,7-Dichloro-1H-indol-2-yl)-(4-methyl-piperazin-1-yl)-methanone.

Further examples of preferred compounds include (6-Chloro-1H-indol-2-yl)-(4-methyl-piperazin-1-yl)-methanone; (1H-Indol-2-yl)-(3-methyl-piperazin-1-yl)-methanone; (7-Bromo-1H-indol-2-yl)-(4-methyl-piperazin-1-yl)-methanone; (5-Bromo-benzofuran-2-yl)-(4-methyl-piperazin-1-yl)-methanone; and (1H-Indol-2-yl)-(4-methyl-piperazin-1-yl)-methanethione.

The most preferred compound is (5-Chloro-1H-indol-2-yl)-(4-methyl-piperazin-1-yl)-methanone.

The disclosed compounds can be prepared according to the next section.

C. Synthesis

The disclosed compounds may be made by combinatorial or traditional organic synthetic methods, as outlined below in Schemes 1–12 and Chemical Examples 1–86, or by analogous reactions.

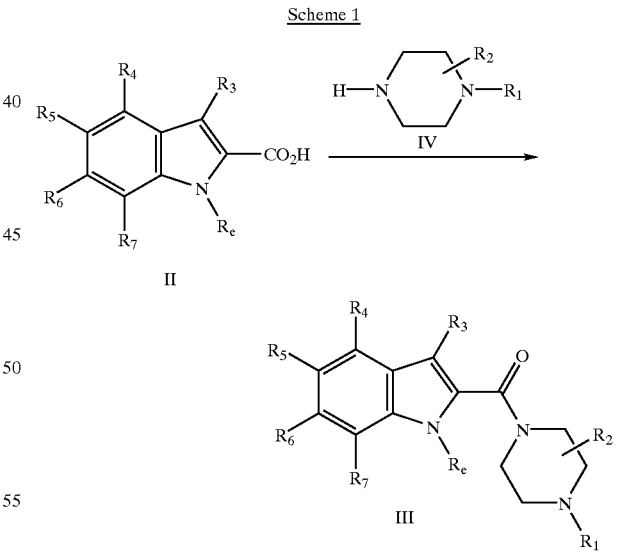

Scheme 1

Compounds of formula III may be prepared from the compounds of formula II using conventional methods of amide bond formation. For example the carboxyl group of compound II may be activated as an active ester, acid chloride, anhydride, mixed anhydride, carbonic mixed anhydride or the like and treated with an amine containing group to give a compound of formula III. For example the compound of formula II may be converted to the corresponding active ester upon treatment with 1-hydroxybenzotriazole in the presence of a carbodiimide for example dicyclohexylcarbodiimide or 1-ethyl-3-(3'-dimethyl-aminopropyl)-carbodiimide hydrochloride in the presence of a base such as triethylamine or N,N-diisopropylethylamine to give a compound of formula III. In a preferred embodiment the compound of formula II is treated with O-(7-azabenzotriazol-1-yl)-N,N,N',N'-tetramethyluroniumhexafluoro-phosphate, (HATU) and 1-hydroxy-7-azabenzotriazole, (HOAT) and N,N-diisopropylethyl-amine in a solvent, for example DMF, THF or the like, together with an amine component IV to give a compound of formula III. In an additional preferred embodiment a compound of formula II may be treated with carbonyldiimidazole (CDI) in a solvent, for example THF, DMF, dichloromethane or the like, followed by an amine component IV to give a compound of formula III.

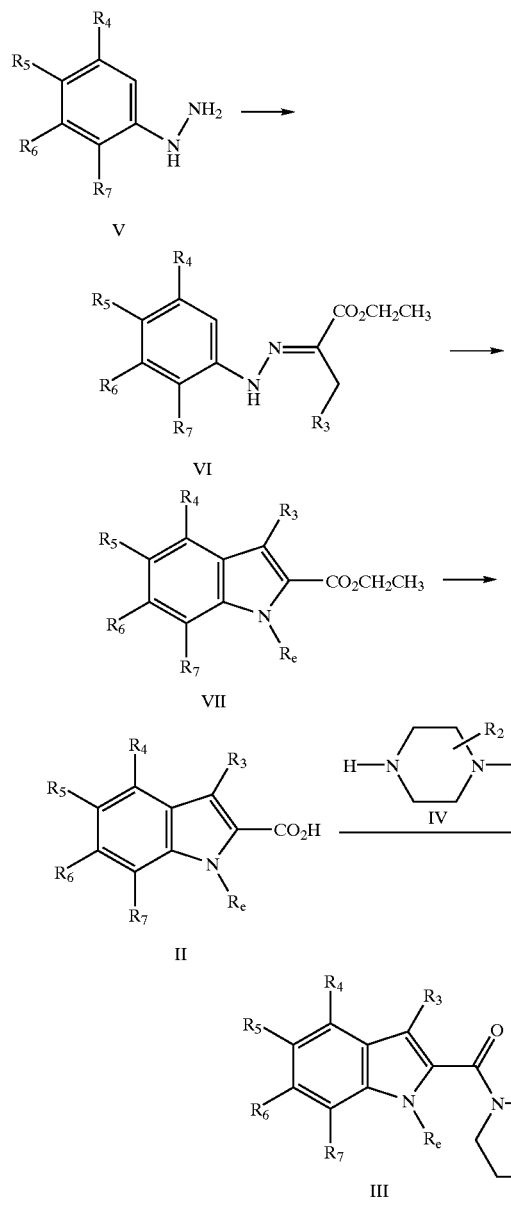

Compounds of formula III may be prepared according to the Fischer-Indole synthesis, which involves the condensation of a phenylhydrazine with an aldehyde or ketone to give an intermediate hydrazone. Thus a compound of formula V may be condensed with ethylpyruvate, usually in the presence of an acid catalyst, for example sulfuric acid to afford a hydrazone of formula VI. Compounds of formula VI may be converted into indoles of formula VII upon treatment with a protic or Lewis acid, if required at elevated temperature, to effect cyclisation. Examples of acids include; polyphosphoric acid, para-toluenesulfonic acid, pyridine hydrochloride, zinc chloride, phosphorus trichloride, polyphosphoric acid trimethylsilyl ester and acetic acid. Compound VI may also be converted to compound VII under thermal conditions by heating a compound of formula VI in a solvent, for example ethylene glycol, tetralin, or the like at elevated temperature, for example at about 150 to 250° C. It will be recognized by one skilled in the art that cyclization of compounds of formula VI to compounds of formula VII can give rise to isomers when compounds of formula V contain substituents. It will be further recognized that the conditions to effect cyclization may be different for different compounds of formula VI.

In a further embodiment, compounds of formula VII may be prepared by condensing an appropriately substituted 2-nitrotoluene with an oxalate di-ester in the presence of a base followed by reduction of the intermediate to afford a compound of formula VII. In a preferred embodiment, a 2-nitrotoluene is condensed with ethylpyruvate in the presence of a base such as sodium methoxide, sodium butoxide, or sodium ethoxide in a solvent such as ethanol, methanol, or butanol. For example, a solution of 2-nitrotoluene in ethanol is heated with ethylpyruvate in the presence of sodium ethoxide at reflux temperature. The condensation product may be converted to a compound of formula VII using a reducing agent, preferably zinc in aqueous acetic acid. Compounds of formula VII may be converted to compounds of formula II using standard methods for ester hydrolysis, for example upon treatment with aqueous acid or base, if necessary at elevated temperature. In a preferred embodiment hydrolysis may be effected upon treating a compound of formula VII with a solution of lithium hydroxide in an alcoholic solvent, preferably ethanol. Compounds of formula II may be converted to compounds of formula III according to the procedures described previously.

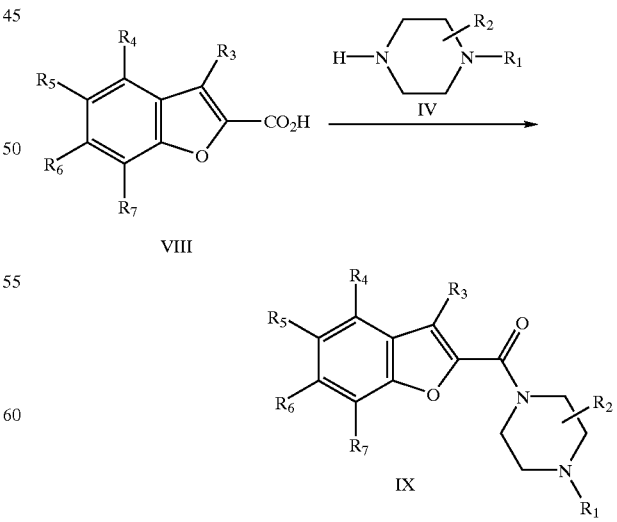

Compounds of formula IX may be prepared from the compounds of formula VIII using conventional methods of amide bond formation as described for the preparation of compounds of formula III from compounds of formula II by condensing the appropriate carboxylic acid of formula VIII with an amine component IV.

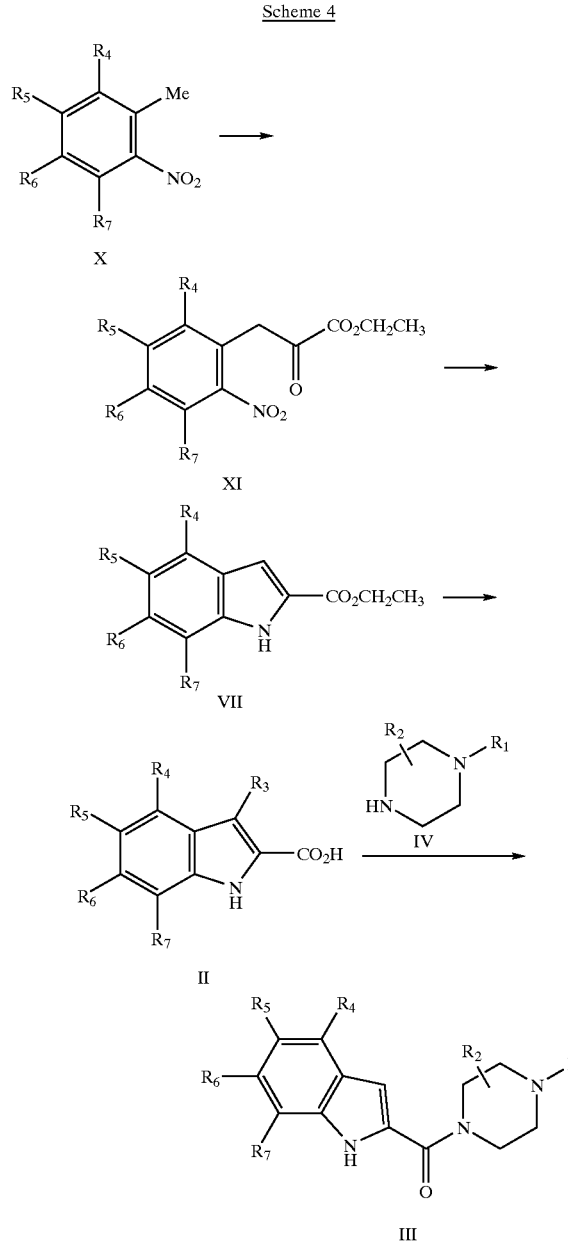

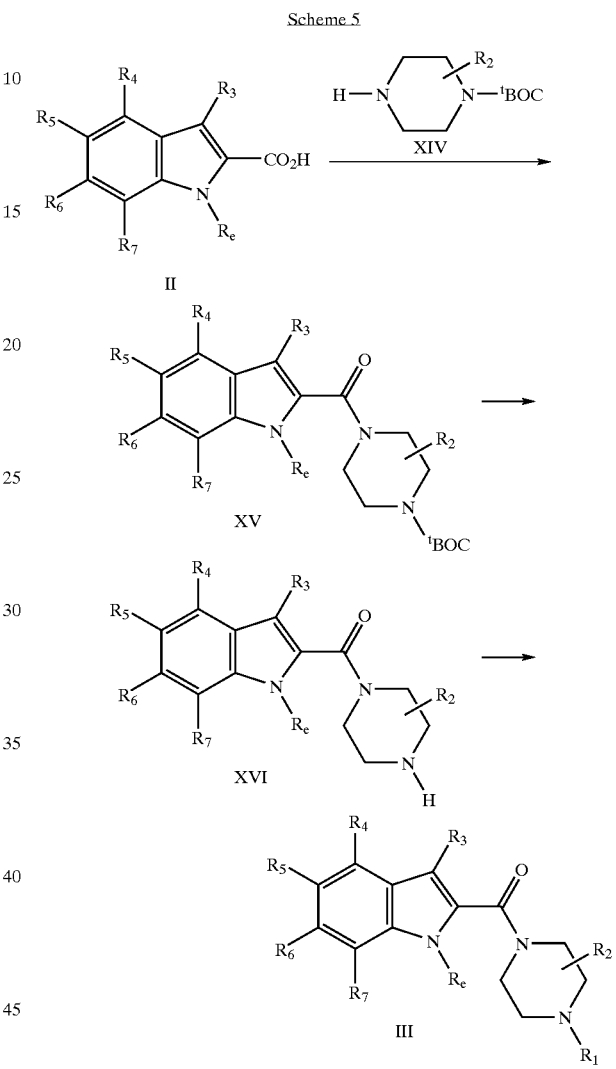

base, if necessary at elevated temperature. In a preferred embodiment hydrolysis may be effected upon treating a compound of formula VII with a solution of lithium hydroxide in THF. Conversion to the target compounds III is effected as described in Scheme 2.

Formulae XII and XIII do not exist in this disclosure.

Compounds of formula III may also be prepared as depicted in Scheme 4. Treatment of an optionally substituted 2-nitrotoluene (formula X) with an oxalate, such as diethyl oxalate, in the presence of a base affords a 2-keto ester of formula XI. Typical bases used to effect this transformation include potassium ethoxide, sodium hydride, and lithium t-butoxide. Reduction of the nitro group of a compound of formula XI to the corresponding aniline is accompanied by cyclization to the indole 2-carboxylate, a compound of formula VII. Typical reductants for this transformation include hydrogen over palladium, tin(II) chloride, and sulfur. Compounds of formula VII may be converted to compounds of formula II using standard methods for ester hydrolysis, for example upon treatment with aqueous acid or Compounds of formula III may be also be prepared from compounds of formula II by condensing a piperazine-1-carboxylic acid tert-butyl ester of formula XIV with a compound of formula II using conventional methods of amide bond formation as described for the preparation of compounds of formula III from compounds of formula II. In a preferred embodiment a compound of formula II is treated with carbonyldiimidazole (CDI) in a solvent, for example THF, DMF, dichloromethane or the like, followed a piperazine-1-carboxylic acid tert-butyl ester of formula XIV to afford a compound of formula XV. Compound XV may be converted to a compound of formula XVI upon treatment with an acid, for example trifluoroacetic acid or hydrochloric acid in a solvent, for example dichloromethane, THF, dioxane or the like. In a preferred embodiment the acid is trifluoroacetic acid and the solvent dichloromethane. A compound of formula III may be obtained from a compound of formula XVI upon treatment with an alkylating agent in the presence of a base. Suitable alkylating agents include, alkylbromides, alkylchlorides, alkyliodides, alkylmesylates, and alkyltosylates. This transformation is effected in the presence of a base, for example potassium carbonate, sodium hydroxide, triethylamine and the like, in a solvent, for example ethanol, methanol, acetone, dichloromethane, DMF, THF and the like. Preferred conditions use potassium carbonate in acetone. The reaction may be carried out at elevated temperature, preferably at about 50° C.

Scheme 6

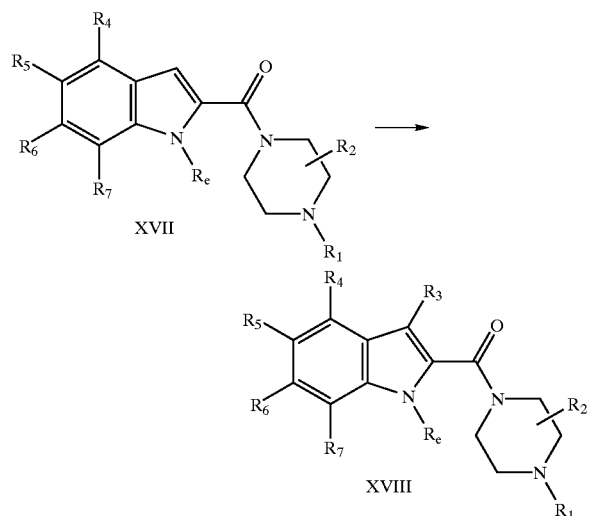

Compounds of formula XVIII may be prepared from compounds of formula XVII according to known methods for the functionalization of the indole nucleus at C-3. Such methods include, but are not limited to; halogenation, for example treatment with a halogen source in a solvent, for example upon treatment with bromine in acetic acid, N-chlorosuccinamide, N-bromosuccinamide, N-iodosuccinamide in dichloromethane, carbontetrachloride, chloroform or the like; formylation, for example by heating a DMF solution of a compound of formula XVII with phosphorus oxychloride (Vilsmeier-Haack conditions); aminoalkylation, for example by treating a compound of formula XVII with a mixture of am amine and a source of formaldehyde (Mannich conditions). One skilled in the art will recognize that not all reactions of indoles with electrophiles will lead to substitution at C-3 alone and that additional substitution may also take place and that mixtures of products may be obtained. It may be further recognized that the products of the substitution reactions (3-substituted indoles) may be used for further transformations.

Scheme 7

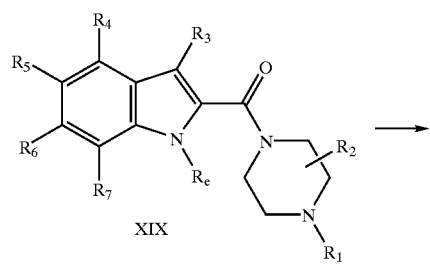

-continued

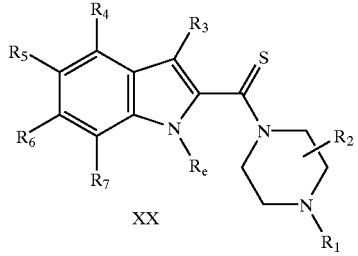

A compound of formula XX may be obtained from a compound of formula XIX upon treatment with 2,4-bis(4-methoxyphenyl)-1,3,2,4-dithiadiphosphetane-2,4-disulfide (also known as Lawesson's reagent) in a solvent for example ether, THF or dioxane. In a preferred embodiment the compound of formula XIX is treated with Lawessons's reagent in THF at ambient temperature to give a compound of formula XX.

Scheme 8

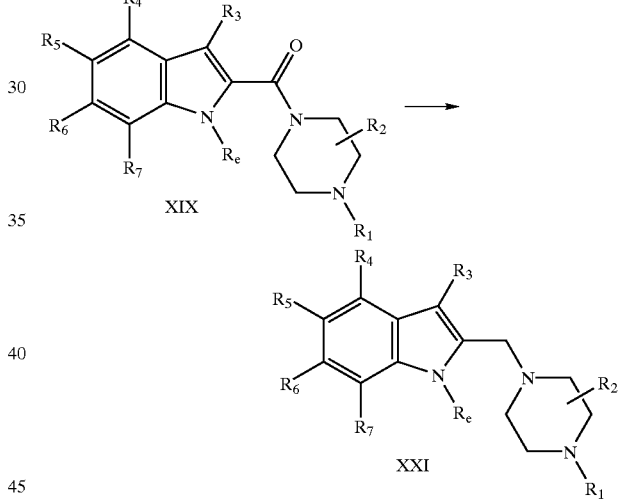

A compound of formula XXI may be obtained from a compound of formula XIX using conventional methods for amide bond reduction. For example using lithium aluminum hydride in THF, magnesium aluminum hydride in THF, lithium trimethoxyaluminum hydride, sodium bis(2-methoxyethoxy)-aluminum hydride, alane in THF and borane or borane-dimethyl sulfide complex in THF. A preferred method is the use of lithium aluminum hydride in a solvent, for example THF, dioxane, ether or the like at from 25° C. to the boiling point of the selected solvent. In a more preferred embodiment the reducing agent is lithium aluminum hydride in THF at reflux temperature. As shown in the scheme below, compounds of formula XI may be prepared by utilizing a Phillips-type reaction that involves the condensation of an ortho-arylene diamine with a carboxcylic acid or the like, to generate the benzimidazole core. Accordingly, a compound of formula XXII may be Scheme 9

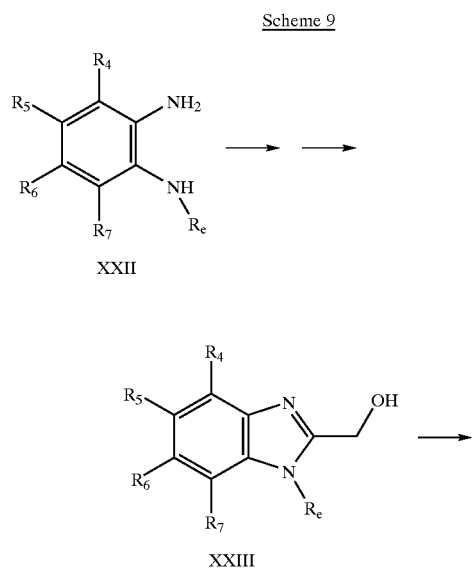

XXII

XXIII

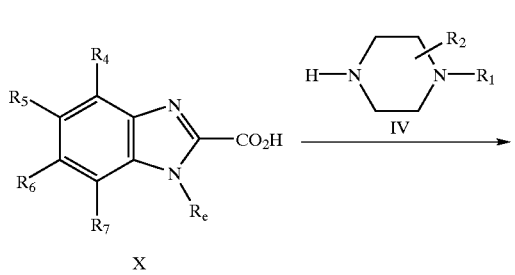

X

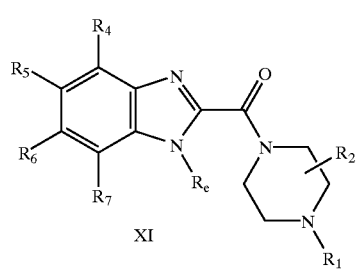

XI condensed with glycolic acid and typically with an acid catalyst, for example hydrochloric acid, to afford compounds of formula XXIII. It will be recognized by one skilled in the art that the condensation of compounds of formula XXII to compounds of formula XXIII can give rise to isomers when compounds of formula XXII contain substituents. Compounds of formula XXIII may be oxidized with a suitable oxidizing agent to give compounds of formula X. Oxidants may include potassium permanganate, chromium trioxide, sodium hypochlorite, dimethyl sulfoxide with oxalyl chloride, manganese dioxide or any combination thereof. Compounds of formula X may be converted to compounds of formula XI according to the procedures described previously for compounds of formula II by condensing the appropriate carboxylic acid of formula X with an amine component IV.

Scheme 10

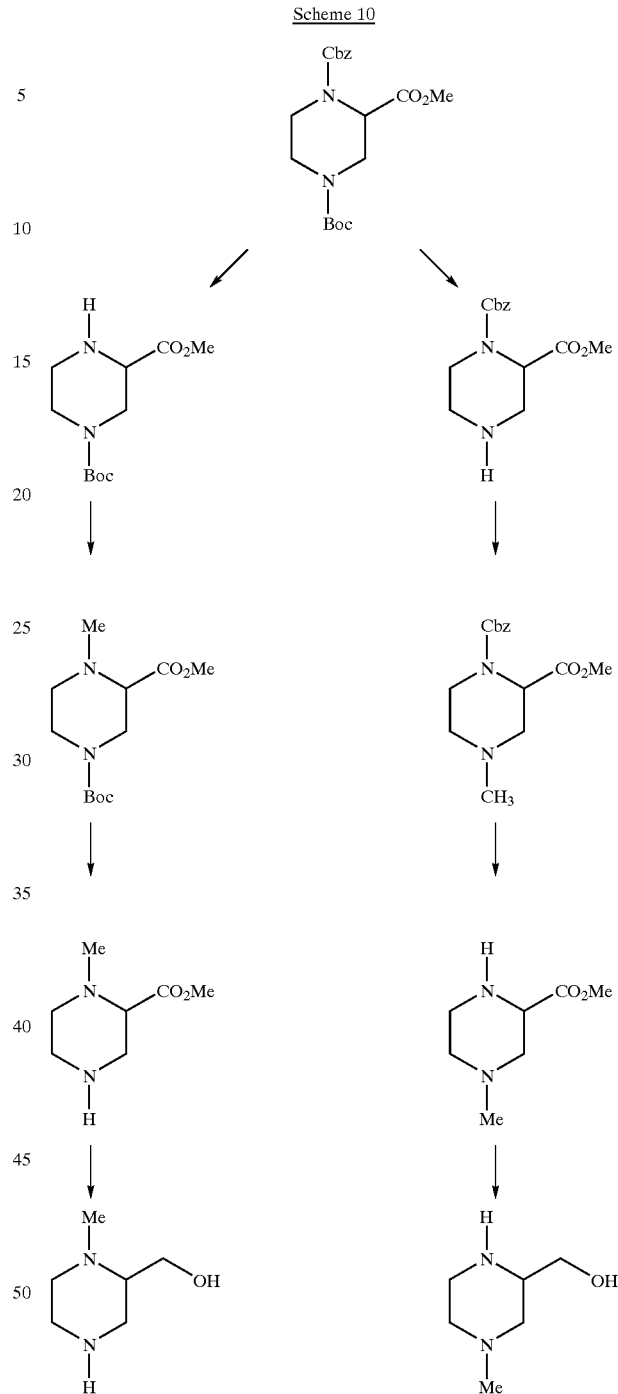

Scheme 10 illustrates methods of making substituted proximal and distal regioisomers. Analogous methods may be used with rings of other than 6 members, such as 5- or 7-membered rings. Further modifications may be made to change the hydroxymethyl and the methyl ester substituents using methods well known to those skilled in the art, including, but not limited to, those methods detailed in Schemes 11 and 12. Piperazine-1,2,4-tricarboxylic acid 1-benzyl ester 4-tert-butyl ester 2-methyl ester can be prepared according to the procedure of Bigge et al. (*Tetrahedron Lett.* 30:5193–5196, 1989). Selective deprotection of either the CBz or the BOC group can be accomplished using standard methods. For example, selective removal of the CBz group of piperazine-1,2,4-tricarboxylic acid 1-benzyl ester 4-tert-butyl ester 2-methyl ester can be accomplished upon treatment with, but not limited to, $H_2$ and Pd/C or ammonium formate and Pd/C in solvents such as ethanol or ethyl acetate or the like, to give piperazine-1,3-dicarboxylic acid 1-tert-butyl ester 3-methyl ester. Conversion of piperazine-1,3-dicarboxylic acid 1-tert-butyl ester 3-methyl ester to 4-methyl-piperazine-1,3-dicarboxylic acid 1-tert-butyl ester 3-methyl ester can be accomplished using standard conditions for reductive amination. These include, but are not limited to, treatment with paraformaldehyde in the presence of a reducing agent such as sodium borohydride, sodium cyanoborohydride or sodium triacetoxyborohydride or the like, in a solvent such as tetrahydrofuran, methanol, ethanol, 1,2-dichloroethane, trifluoroethanol, or the like. One skilled in the art will recognize that addition of acid to decrease the pH of the reaction mixture to a pH of less than about 7 may be necessary to effect reaction, wherein the acid is added as needed and is such as acetic acid, hydrochloric acid, and the like. Preferred reducing agents are sodium cyanoborohydride or sodium triacetoxyborohydride. Removal the the BOC group can be accomplished upon treatment with an acid, for example trifluoroacetic acid or hydrochloric acid in a solvent, for example dichloromethane, THF, dioxane or the like to give 1-methyl-piperazine-2-carboxylic acid methyl ester. Reduction of the methyl ester can be accomplished using standard conditions including, but not limited to, treatment with reducing agents such as lithium aluminum hydride or diisobutylaluminum hydride or the like, in solvents such as THF or diethyl ether or the like to afford (1-methyl-piperazin-2-yl)-methanol.

Alternatively, selective removal of the BOC group of piperazine-1,2,4-tricarboxylic acid 1-benzyl ester 4-tert-butyl ester 2-methyl ester can be accomplished upon treatment with an acid, for example trifluoroacetic acid or hydrochloric acid in a solvent, for example dichloromethane, THF, dioxane or the like to give piperazine-1,2-dicarboxylic acid 1-benzyl ester 2-methyl ester. Conversion of piperazine-1,2-dicarboxylic acid 1-benzyl ester 2-methyl ester to 4-methyl-piperazine-1,2-dicarboxylic acid 1-benzyl ester 2-methyl ester can be accomplished using standard conditions for reductive amination. These include, but are not limited to, treatment with paraformaldehyde in the presence of a reducing agent such as sodium borohydride, sodium cyanoborohydride or sodium triacetoxyborohydride, or the like, in a solvent such as tetrahydrofuran, methanol, ethanol, 1,2-dichloroethane, trifluoroethanol, or the like. One skilled in the art will recognize that addition of acid to decrease the pH of the reaction mixture to a pH of less than about 7 may be necessary to effect reaction, wherein the acid is added as needed and is such as acetic acid, hydrochloric acid, or the like. Preferred reducing agents are sodium cyanoborohydride or sodium triacetoxyborohydride. Removal of the CBz group of 4-methyl-piperazine-1,2-dicarboxylic acid 1-benzyl ester 2-methyl ester can be accomplished upon treatment with, but not limited to, $H_2$ and Pd/C or ammonium formate and Pd/C in sovents such as ethanol or ethyl acetate or the like, to give 4-methyl-piperazine-2-carboxylic acid methyl ester. Reduction of the methyl ester can be accomplished using standard conditions including, but not limited to, treatment with reducing agents such as lithium aluminum hydride or diisobutylaluminum hydride or the like, in solvents such as THF or diethyl ether or the like, to afford (4-methyl-piperazin-2-yl)-methanol.

Scheme 11

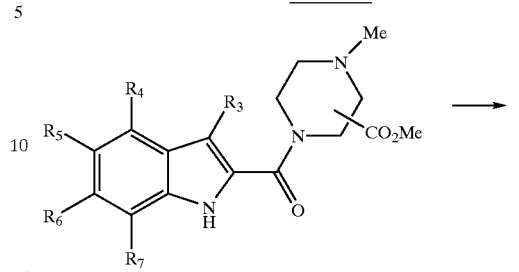

XXIV

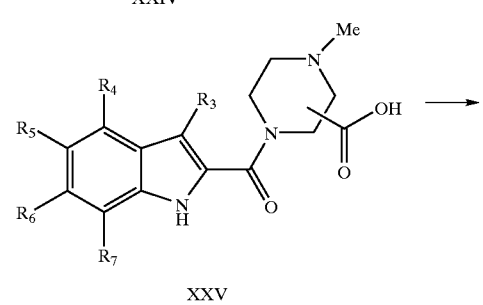

XXV

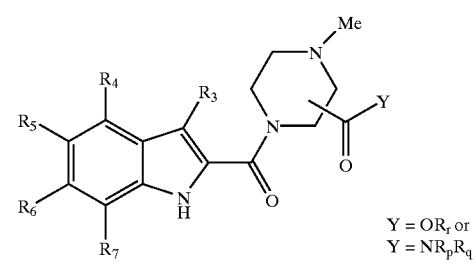

$Y = OR_r$ or
$Y = NR_pR_q$

XXVI

Scheme 12

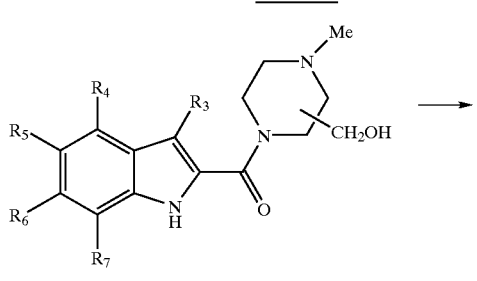

XXVII

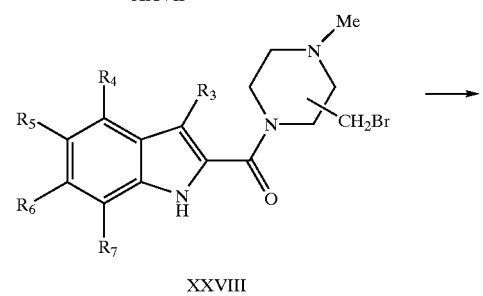

XXVIII

-continued

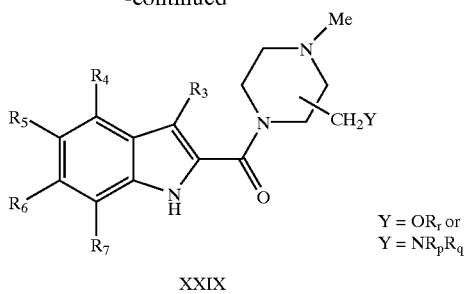

XXIX

Compounds of formulas XXIV and XXVII may be prepared from compounds of formula II using conventional methods of amide bond formation, as described for the preparation of compounds of formula III from compounds of formula II, by condensing the appropriate carboxylic acid of formula II with an amine component such as those described in Scheme 10. Schemes 11 and 12 illustrate non-limiting methods for providing the substituted rings, such as the substituted piperazines shown in compounds XXVI and XXIX. For Scheme 11, hydrolysis of the ester can be accomplished using standard methods for ester hydrolysis, for example upon treatment with aqueous acid or base, if necessary at elevated temperature. Compounds of formula XXVI where Y is nitrogen can be prepared using conventional methods of amide bond formation, as described for the preparation of compounds of formula III from compounds of formula II, by condensing the appropriate carboxylic acid of formula XXV with a suitable amine component. Compounds of formula XXVI where Y is oxygen can be prepared using conventional methods of ester formation such as, but not limited to, conversion to the acid chloride using reagents such as oxalyl chloride, or the like, followed by treatment with an appropriate alcohol. For Scheme 12, compounds of formula XXVIII can be prepared from compounds of formula XXVII using conventional methods such as, but not limited to, treatment with triphenylphosphine and carbon tetrabromide, thionyl bromide or HBr. Compounds of formula XXVIII may be treated with alcohols or amines to afford compounds of formula XXIX where Y is oxygen or nitrogen respectively, possibly in the presence of a suitable base such as, but not limited to, cesium carbonate or triethylamine.

D. Uses

According to the invention, the disclosed compounds and compositions are useful for the amelioration of symptoms associated with, the treatment of, and the prevention of, the following conditions and diseases: inflammatory disorders, asthma, atherosclerosis, psoriasis, rheumatoid arthritis, ulcerative colitis, Crohn's disease, inflammatory bowel disease, multiple sclerosis, allergic disorders, dermatological disorders, autoimmune disease, lymphatic disorders, and immunodeficiency disorders. The disclosed compounds may also be useful as adjuvants in chemotherapy or in the treatment of itchy skin. The invention also features pharmaceutical compositions that include, without limitation, one or more of the disclosed compounds, and pharmaceutically acceptable carrier or excipient.

Aspects of the invention include (a) a pharmaceutical composition comprising a compound of formula (I) or (Ib), or one or more preferred compounds as described herein, and a pharmaceutically acceptable carrier; (b) a packaged drug comprising (1) a pharmaceutical composition comprising a compound of claim 1, 2, or 3 and a pharmaceutically acceptable carrier, and (2) instructions for the administration of said composition for the treatment or prevention of an $H_4$-mediated disease or condition.

The invention also provides a method for treating an $H_4$-mediated condition in a patient, said method comprising administering to the patient a pharmaceutically effective amount of a composition comprising a compound of formula (I) or (Ib) or other disclosed or preferred compounds. For example, the invention features a method for treating an $H_4$ mediated condition in a patient, said method comprising administering to the patient a pharmaceutically effective $H_4$-antagonizing amount of a composition comprising a compound of formula (I) or (Ib) or other disclosed or preferred compounds.

The effect of an antagonist may also be produced by an inverse agonist. Inverse agonism describes the property of a compound to actively turn off a receptor that displays constitutive activity. Constitutive activity can be identified in cells that have been forced to over-express the human $H_4$ receptor. Constitutive activity can be measured by examining cAMP levels or by measuring a reporter gene sensitive to cAMP levels after a treatment with a cAMP-stimulating agent such as forskolin. Cells that over-express $H_4$ receptors will display lower cAMP levels after forskolin treatment than non-expressing cells. Compounds that behave as $H_4$ agonists will dose-dependently lower forskolin-stimulated cAMP levels in $H_4$-expressing cells. Compounds that behave as inverse $H_4$ agonists will dose-dependently stimulate cAMP levels in $H_4$-expressing cells. Compounds that behave as $H_4$ antagonists will block either $H_4$ agonist-induced inhibition of cAMP or inverse $H_4$ agonist-induced increases in cAMP.

Further embodiments of the invention include disclosed compounds that are inhibitors of a mammalian histamine $H_4$ receptor function, inhibitors of inflammation or inflammatory responses in vivo or in vitro, modulators of the expression of a mammalian histamine $H_4$ receptor protein, inhibitors of polymorphonuclear leukocyte activation in vivo or in vitro, or combinations of the above, and corresponding methods of treatment, prophylaxis, and diagnosis comprising the use of a disclosed compound.

1. Dosages

Those skilled in the art will be able to determine, according to known methods, the appropriate dosage for a patient, taking into account factors such as age, weight, general health, the type of symptoms requiring treatment, and the presence of other medications. In general, an effective amount will be between 0.01 and 1000 mg/kg per day, preferably between 0.5 and 300 mg/kg body weight, and daily dosages will be between 10 and 5000 mg for an adult subject of normal weight. Capsules, tablets or other formulations (such as liquids and film-coated tablets) may be of between 0.5 and 200 mg, such as 1, 3, 5, 10, 15, 25, 35, 50 mg, 60 mg, and 100 mg and can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

3. Related Compounds

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$ alkyl, cycloalkyl, aryl, heteroaryl, or non-aromatic heterocyclic) amino acid addition salts, esters, and amides that are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1–19, which is incorporated herein by reference. Representative pharmaceutically acceptable amides of the invention include those derived from ammonia, primary $C_{1-6}$ alkyl amines and secondary di ($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

The invention also includes disclosed compounds having one or more functional groups (e.g., hydroxyl, amino, or carboxyl) masked by a protecting group. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4', 4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4- dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Protection for 1,2- and 1,3-Diols

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of Amides Include

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl) propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Examples of Special NH Protective Groups Include

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3- pyrrolin-3-yl), quaternary ammonium salts, N-benzyl, N-di (4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N-(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of acyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or —S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrozones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substitued Methylene Derivatives, Cyclic Derivatives

Examples of substituted methylene and cyclic derivatives include oxazolidines, 1-methyl-2-(1'-hydroxyalkyl)imidazoled, N,N'-dimethylimidazolidines, 2,3-dihydro-1,3-benzothiazoles, diethylamine adducts, and methylaluminum bis(2,6-di-t-butyl-4-methylphenoxide)(MAD)complex.

Monoprotection of Dicarbonyl Compounds

Selectives Protection of α- and β-Diketones

Examples of selective protection of α- and β-diketones include enamines, enol acetates, enol ethers, methyl, ethyl, i-butyl, piperidinyl, morpholinyl, 4-methyl-1,3-dioxolanyl, pyrrolidinyl, bezyl, S-butyl, and trimethylsilyl.

Cyclic Ketals, Monothio and Dithio Ketals

Examples of cyclic ketals, monothio and dithio ketals include bismethylenedioxy derivatives and tetramethylbis-methylenedioxy derivates.

Protecton for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl.

E. CHEMICAL EXAMPLES

Example 1

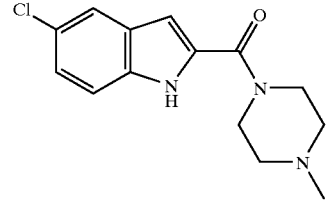

$K_i = 0.005$ μM (5-Chloro-1H-indol-2-yl)-(4-methyl-piperazin-1-yl)-methanone

A mixture of 5-chloroindole-2-carboxylic acid (0.234 g), HATU (0.569 g), HOAT (0.203 g) and N,N- diisopropylethylamine (0.191 mL) in DMF (0.6 mL) was treated with N-methylpiperazine (0.1 mL) stirred at ambient temperature for 48 h then concentrated under reduced pressure. The residue was dissolved in ethyl acetate, washed with 1 M hydrochloric acid, saturated sodium hydrogen carbonate solution and then brine, dried over sodium sulfate, filtered, and concentrated under reduced pressure. The residue was purified via silica gel chromatography (3–10% 2 M ammonia in methanol/dichloromethane) to give the title compound (0.18 g). $^1$H NMR (400 MHz, CDCl$_3$): δ 9.60 (br s, 1H), 7.65 (d, J=1.5 Hz, 1H), 7.40 (d, J=8.6 Hz, 1H), 7.29 (d, J=2.0 Hz, 1H), 7.26 (d, 1.8 Hz, 1H), 6.76 (d, J=1.5 Hz, 1H), 4.0 (br m, 4H), 2.56 (t, J=5.1 Hz, 4H), 2.41 (s, 3H). Analysis: Calc'd for C$_{14}$H$_{16}$ClN$_3$O; C, 60.54; H, 5.81; N, 15.13; Found: C, 59.99; H, 5.94; N, 18.87.

The title compounds of the following examples (2–14) were prepared according to the general procedure of Scheme 1, as indicated for Example 1.

Example 2

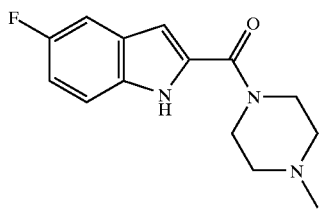

$K_j$ = 0.018 μM (5-Fluoro-1H-indol-2-yl)-(4-methyl-piperazin-1-yl)-methanone $^1$H NMR (400 MHz, CDCl$_3$): δ 9.70 (br s, 1H), 7.33 (m, 2H), 7.09–6.98 (m, 1H), 6.75 (m, 1H), 3.97 (br m, 4H), 2.53 (dm, J=4.7 Hz, 4H), 2.38 (s, 3H).

Example 3

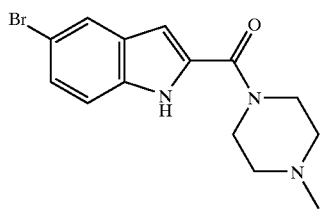

$K_j$ = 0.008 μM (5-Bromo-1H-indol-2-yl)-(4-methyl-piperazin-1-yl)-methanone $^1$H NMR (400 MHz, CDCl$_3$): δ 9.65 (br s, 1H), 7.78 (d, J=1.0 Hz, 1H), 7.40–7.26 (m, 2H), 6.73 (d, J=2.3 Hz, 1H), 3.97 (br m, 4H), 2.53 (t, J=5.1 Hz, 4H), 2.37 (s, 3H).

Example 4

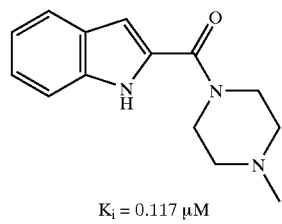

$K_i$ = 0.117 μM (1H-Indol-2-yl)-(4-methyl-piperazin-1-yl)-methanone $^1$H NMR (400 MHz, CDCl$_3$/CD$_3$OD): δ 7.63–7.56 (m, 1H), 7.40 (dt, J=1.0, 8.3 Hz, 1H), 7.26–7.20 (m, 1H), 7.11–7.05 (m, 1H), 6.99 (d, J=0.8 Hz), 6.72 (d, J=0.8 Hz), 3.88 (br m, 4H), 2.48 (t, J=5.1 Hz, 4H), 2.31 (s, 3H).

Example 5

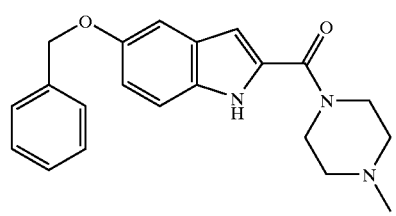

Kj = 7 μM (5-Benzyloxy-1H-indol-2-yl)-(4-methyl-piperazin-1-yl)-methanone

Example 6

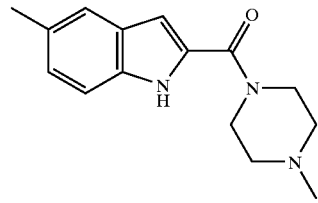

$K_j$ = 0.011 μM (5-Methyl-1H-indol-2-yl)-(4-methyl-piperazin-1-yl)-methanone $^1$H NMR (400 MHz, CDCl$_3$): δ 8.91 (br s, 1H), 7.34 (dm, J=0.7 Hz, 1H), 7.24 (d, J=8.3 Hz, 1H), 7.04 (dd, J=8.3, 1.3 Hz, 1H), 6.62 (dd, J=2.0, 0.8 Hz, 1H), 3.88 (br m, 4H), 2.44 (t, J=4.0 Hz, 4H), 2.37 (s, 3H), 2.29 (s, 3H).

Example 7

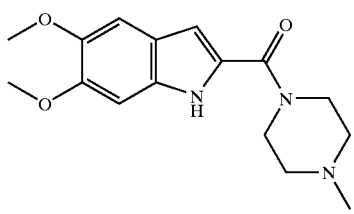

K$_i$ = 10 µM (5,6-Dimethoxy-1H-indol-2-yl)-(4-methyl-piperazin-1-yl)-methanone

Example 8

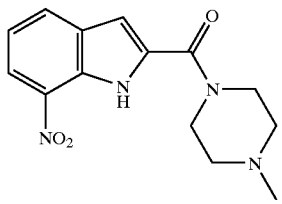

K$_i$ = 2 µM (4-Methyl-piperazin-1-yl)-(7-nitro-1H-indol-2-yl)-methanone $^1$H NMR (400 MHz, CDCl$_3$): δ 10.46 (br s, 1H), 8.29 (d, 1H), 8.06 (d, 1H), 7.34 (m, 1H), (t, 1H), 3.94 (br m, 4H), 2.54 (t, 4H), 2.40 (s, 3H).

Example 9

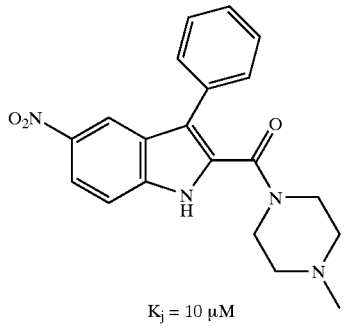

K$_i$ = 10 µM (4-Methyl-piperazin-1-yl)-(5-nitro-3-phenyl-1H-indol-2-yl)-methanone

Example 10

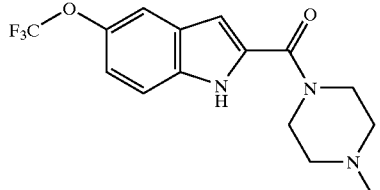

K$_i$ = 1.7 µM (4-Methyl-piperazin-1-yl)-(5-trifluoromethoxy-1H-indol-2-yl)-methanone

Example 11

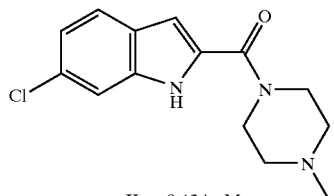

K$_i$ = 0.124 µM (6-Chloro-1H-indol-2-yl)-(4-methyl-piperazin-1-yl)-methanone $^1$H NMR (400 MHz, CDCl$_3$): δ 10.14 (br s, 1H), δ 7.55 (d, J=8.3 Hz, 1H), 7.44 (t, J=1.0 Hz, 1H), 7.10 (dd, J=8.3, 1.8 Hz, 1H), 6.76 (dd, J=2.3, 1.0 Hz, 1H), 4.00 (br m, 4H), 2.54 (t, J=5.1 Hz, 4H), 2.38 (s, 3H). MS: exact mass calculated for C$_{14}$H$_{16}$ClN$_3$O, 277.10; m/z found, 278.1 [M+H]$^+$.

Example 12

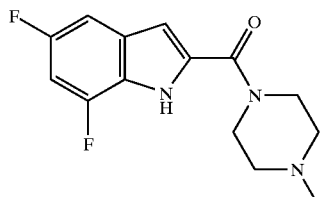

K$_i$ = 0.019 µM (5,7-Difluoro-1H-indol-2-yl)-(4-methyl-piperazin-1-yl)-methanone $^1$H NMR (400 MHz, CDCl$_3$): δ 9.94 (br s, 1H), 7.10 (dd, J=8.8, 2.0 Hz, 1H), 6.87–6.78 (m, 1H), 6.77 (t, J=2.8 Hz, 1H), 3.97 (br m, 4H), 2.53 (t, J=5.1 Hz, 4H), 2.37 (s, 3H). MS: exact mass calculated for C$_{14}$H$_{15}$F$_2$N$_3$O, 279.12; m/z found, 280 [M+H]$^+$.

Example 13

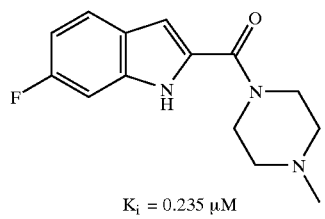

$K_i$ = 0.235 μM (6-Fluoro-1H-indol-2-yl)-(4-methyl-piperazin-1-yl)-methanone $^1$H NMR (400 MHz, CDCl$_3$): δ 9.45 (br s, 1H), 7.49 (dd, J=8.8, 5.6 Hz, 1H), 7.02 (dd, J=, 9.4, 2.3 Hz, 1H), 6.87–6.81 (m, 1H), 6.69 (dd, J=2.0, 1.0 Hz, 1H), 3.89 (br m, 4H), 2.44 (t, J=5.1 Hz, 4H), 2.88 (s, 3H).

Example 14

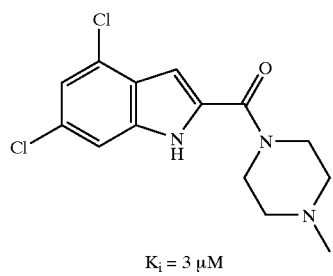

$K_i$ = 3 μM (4,6-Dichloro-1H-indol-2-yl)-(4-methyl-piperazin-1-yl)-methanone

Example 15

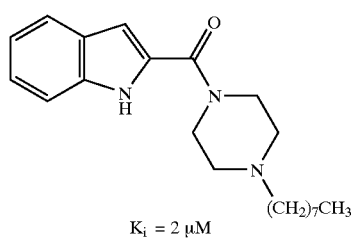

$K_i$ = 2 μM (1H-Indol-2-yl)-(4-octyl-piperazin-1-yl)-methanone

Indole-2-carboxylic acid (0.193 g) in THF (25 mL) was treated with carbonyldiimidazole (0.178 g) and stirred at ambient temperature for 2 h whereupon 1-octyl-piperazine (0.142 g) was added. The mixture was stirred at ambient temperature for 18 h, and the solvent removed under reduced pressure. The residue was dissolved in ethyl acetate and washed with saturated sodium bicarbonate solution, and the organic portion was separated, dried over soduim sulfate and filtered. Solvent was evaporated to afford the title compound (0.28). $^1$H NMR (400 MHz, CD$_3$OD): δ 7.50 (d, J=8.0 Hz, 1H), 7.32 (d, J=8.3 Hz, 1H), 7.13–7.09 (m, 1H), 6.98–6.94 (m, 1H), 6.71 (s, 1H), 3.79 (s, 4H), 2.46 (t, J=4.7 Hz, 4H), 2.32 (t, J=7.7 Hz, 2H), 1.46 (br s, 2H), 1.36–1.03 (m, 12H), 0.82–0.79 (m, 3H).

The title compounds of the following examples (16–38) were prepared according to the general procedure of Scheme 1, as indicated for Example 15.

Example 16

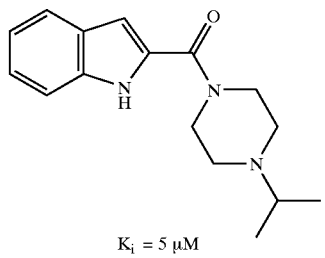

$K_i$ = 3 μM (4-Ethyl-piperazin-1-yl)-(1H-indol-2-yl)-methanone

Example 17

$K_i$ = 5 μM (1H-Indol-2-yl)-(4-isopropyl-piperazin-1-yl)-methanone

Example 18

$K_i$ = 5 μM

[4-(3-Dimethylamino-propyl)-piperazin-1-yl]-(1H-indol-2-yl)-methanone

Example 19

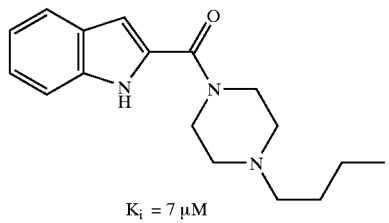

$K_i$ = 7 μM

| 33 | 34 |
|---|---|
| (4-Butyl-piperazin-1-yl)-(1H-indol-2-yl)-methanone | (1H-Indol-2-yl)-[4-(2-piperazin-1-yl-ethyl)-piperazin-1-yl]-methanone |

Example 20

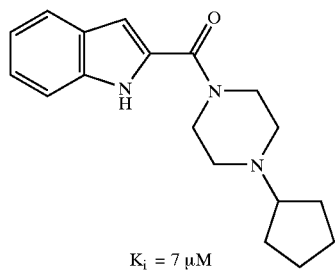

$K_i = 7\ \mu M$ (4-Cyclopentyl-piperazin-1-yl)-(1H-indol-2-yl)-methanone

Example 21

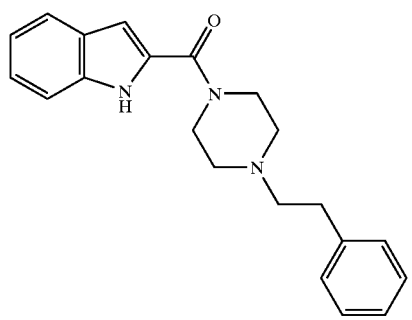

$K_j = 7\ \mu M$ (1H-Indol-2yl)-(4-phenethyl-piperazin-1-yl)-methanone

Example 22

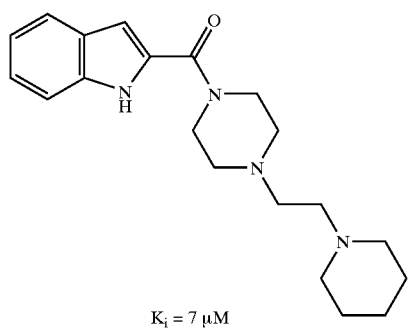

$K_i = 7\ \mu M$

Example 23

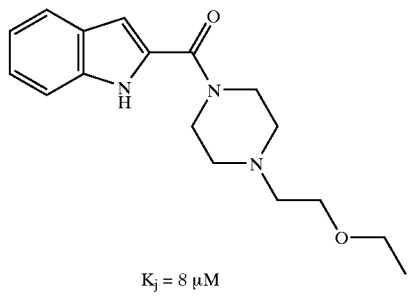

$K_j = 8\ \mu M$

[4-(2-Ethoxy-ethyl)-piperazin-1-yl]-(1H-indol-2-yl)-methanone

Example 24

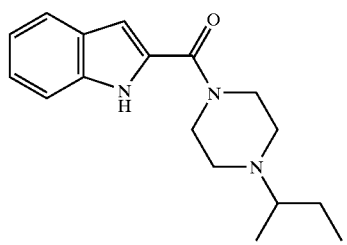

$K_j = 8\ \mu M$ (4-sec-Butyl-piperazin-1-yl)-(1H-indol-2-yl)-methanone

Example 25

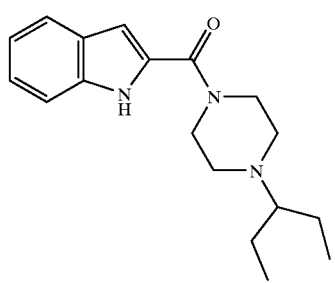

$K_i = 8\ \mu M$

[4-(1-Ethyl-propyl)-piperazin-1-yl]-(1H-indol-2-yl)-methanone

Example 26

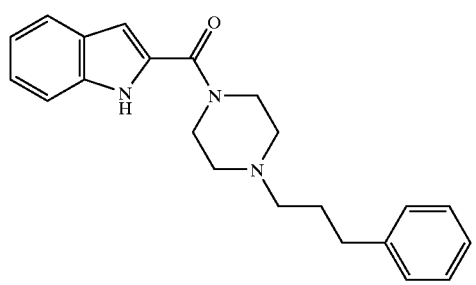

$K_j = 8\ \mu M$ (1H-Indol-2-yl)-[4-(3-phenyl-propyl)-piperazin-1-yl]-methanone

Example 27

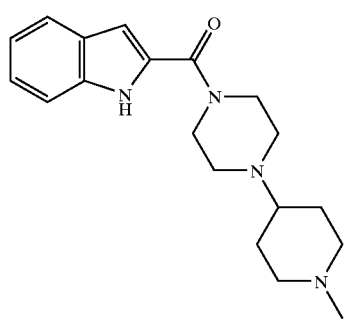

$K_j = 8\ \mu M$ (1H-Indol-2-yl)-[4-(1-methyl-piperidin-4-yl)-piperazin-1-yl]-methanone Example 28

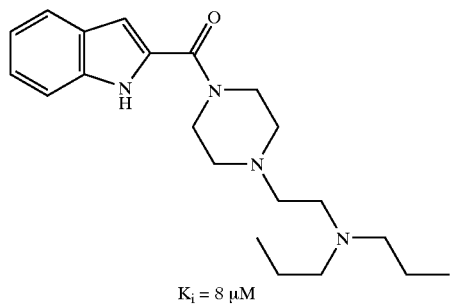

$K_i = 8\ \mu M$

[4-(2-Dipropylamino-ethyl)-piperazin-1-yl]-(1H-indol-2-yl)-methanone

Example 29

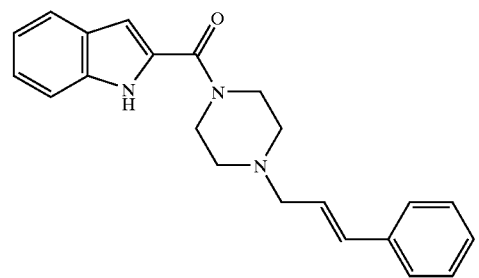

$K_j = 10\ \mu M$ (1H-Indol-2-yl)-[4-(3-phenyl-allyl)-piperazin-1-yl]-methanone

Example 30

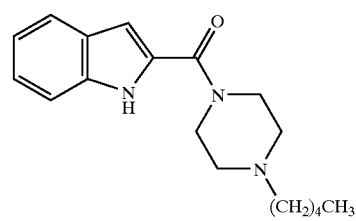

$K_j = 9\ \mu M$ (1H-Indol-2-yl)-(4-pentyl-piperazin-1-yl)-methanone

Example 31

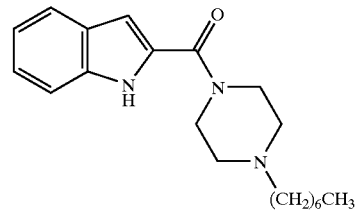

$K_j = 9\ \mu M$

37

(4-Heptyl-piperazin-1-yl)-(1H-indol-2-yl)-methanone

Example 32

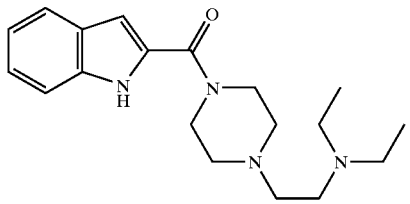

$K_i = 9 \mu M$

[4-(2-Diethylamino-ethyl)-piperazin-1-yl]-(1H-indol-2-yl)-methanone

Example 33

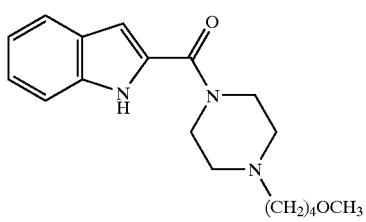

$K_i = 9 \mu M$ (1H-Indol-2-yl)-[4-(4-methoxy-butyl)-piperazin-1yl]-methanone

Example 34

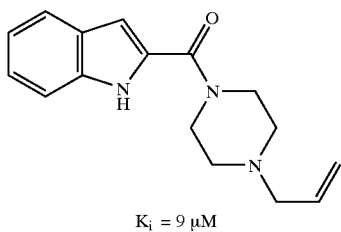

$K_i = 9 \mu M$ (4-Allyl-piperazin-1-yl)-(1H-indol-2yl)-methanone

Example 35

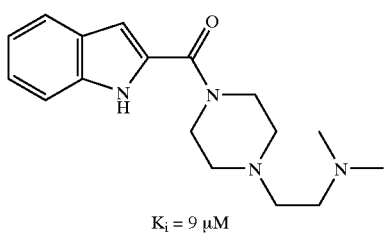

$K_i = 9 \mu M$

38

[4-(2-Dimethylamino-ethyl)-piperazin-1-yl]-(1H-indol-2-yl)-methanone

Example 36

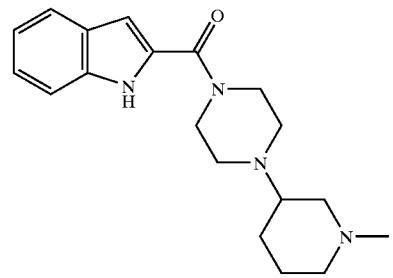

$K_i = 10 \mu M$ (1H-Indol-2-yl)-[4-(1-methyl-piperadin-3-yl)-piperazin-1yl]-methanone Example 37

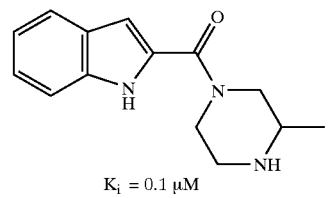

$K_i = 0.1 \mu M$ (1H-Indol-2-yl)-(3-methyl-piperazin-1-yl)-methanone $^1$H NMR (400 MHz, CDCl$_3$): δ 9.16 (s, 1H), 7.65 (d, J=7.9 Hz, 1H), 7.42 (d, J=8.3 Hz, 1H), 7.30–7.25 (m, 1H), 7.14 (t, J=7.2 Hz, 1H), 6.77 (s, 1H), 4.59 (m, 2H), 3.10 (m, 1H), 2.94–2.86 (m, 2H), 1.65 (s, 3H), 1.14 (d, J=5.6 Hz, 3H).

Example 38

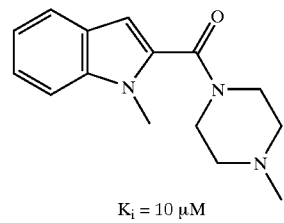

$K_i = 10 \mu M$ (1-Methyl-1H-indol-2-yl)-(4-methyl-piperazin-1-yl)-methanone $^1$H NMR (400 MHz, CDCl$_3$): δ 7.64 (dt, J=1.0, 7.8 Hz, 1H), 7.38 (dd, J=8.3, 0.8 Hz, 1H), 7.35–7.32 (m, 1H), 7.19–7.14 (m, 1H), 6.62 (d, J=0.8 Hz, 1H), 3.86 (s, 3H), 3.83 (br m, 4H), 2.49 (br m, 4H), 2.37 (s, 3H).

Example 39

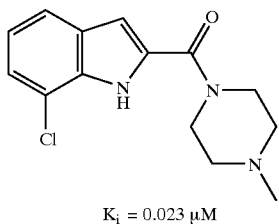

$K_i = 0.023 \mu M$ (7-Chloro-1H-indol-2-yl)-(4-methyl-piperazin-1-yl)-methanone 2-Chlorophenylhydrazine hydrochloride (0.5 g) in ethanol (25 mL) was treated with ethylpyruvate (0.324 g) and concentrated sulfuric acid (3 drops). The mixture was stirred at ambient temperature for five min and treated with polyphosphoric acid (0.5 g). The mixture was heated at reflux temperature for 24 h whereupon additional polyphosphoric acid (0.5 g) was added and heating continued for a further 48 h. The reaction mixture was cooled to ambient temperature and concentrated under reduced pressure. The residue was partitioned between ethyl acetate and water and the pH of the aqueous layer adjusted to neutrality by addition of saturated sodium hydrogen carbonate solution. The organic fraction was separated, washed with brine, dried over magnesium sulfate, filtered, and concentrated. The residue was purified via silica gel chromatography (5–10% ethyl acetate/hexane) to give 7-Chloro-1H-indole-2-carboxylic acid ethyl ester (0.227 g). This material (0.102 g) was used without further purification. The ester was treated with 1 M lithium hydroxide in ethanol (5 mL) followed by water (3 mL) and stirred at ambient temperature for 18 h. The solution was acidified with 10% hydrochloric acid, diluted with water and extracted with ethyl acetate. The organic extracts were washed with brine, dried over magnesium sulfate, filtered, and concentrated to afford give 7-Chloro-1H-indole-2-carboxylic acid (0.089 9). This material (0.089 g), was treated with HATU (0.259 g), HOAT (0.093 g), N,N-diisopropylethylamine (0.158 mL) and N-methylpiperazine (0.05 mL) in DMF (0.6 mL) and stirred at ambient temperature for 18 h. The reaction mixture was concentrated under reduced pressure. The residue was dissolved in ethyl acetate, washed with 1 M hydrochloric acid, saturated sodium hydrogencarbonate solution and then brine, dried over magnesium sulfate, filtered, and concentrated under reduced pressure. The residue was purified via silica gel chromatography (2–10% 2 M ammonia in methanol/dichloromethane) to give the title compound (0.56 9). $^1$H NMR (400 MHz, CDCl$_3$): δ 9.17 (br s, 1H), 7.47 (d, J=8.1 Hz, 1H), 7.21 (dd, J=7.6, 0.8 Hz, 1H), 7.01 (t, J=7.8 Hz, 1H), 6.73 (d, J=2.3 Hz, 1H), 3.88 (br m, 4H), 2.45 (t, J=5.1 Hz, 4H), 2.29 (s, 3H).

The title compounds of the following examples (40–43) were prepared according to the general procedure of Scheme 2, as indicated for example 39.

Example 40

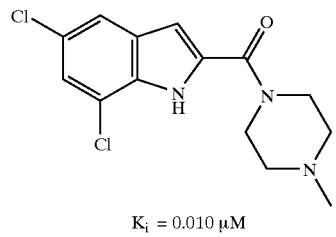

$K_i = 0.010 \mu M$ (5,7-Dichloro-1H-indol-2-yl)-(4-methyl-piperazin-1-yl)-methanone $^1$H NMR (400 MHz, CDCl$_3$): δ 9.08 (br s, 1H), 7.36 (dd, J=1.8, 0.8 Hz, 1H), 7.12 (d, J=1.8 Hz, 1H), 6.56 (d, J=2.3 Hz, 1H), 3.77 (br m, 4H), 2.34 (t, J=5.1 Hz, 4H), 2.20 (s, 3H).

Example 41

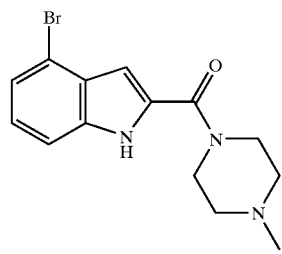

$K_i = 0.040 \mu M$ (4-Bromo-1H-indol-2-yl)-(4-methyl-piperazin-1-yl)-methanone

Example 42

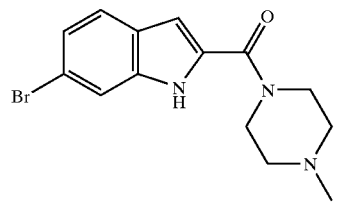

$K_i = 0.188 \mu M$ (6-Bromo-1H-indol-2-yl)-(4-methyl-piperazin-1-yl)-methanone $^1$H NMR (400 MHz, CDCl$_3$): δ 9.70 (br s, 1H), 7.69 (t, J=0.8 Hz, 1H), 7.51 (d, J=8.6 Hz, 1H), 7.24 (dd, J=8.6, 1.8 Hz, 1H), 6.76 (dd, J=2.0, 1.0 Hz, 1H), 3.98 (br m, 4H), 2.54 (t, J=5.1 Hz, 4H), 2.37 (s, 3H).

Example 43

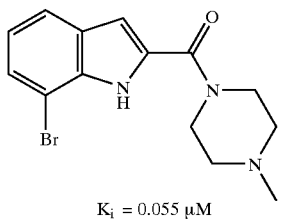

$K_i = 0.055 \, \mu M$ (7-Bromo-1H-indol-2-yl)-(4-methyl-piperazin-1-yl)-methanone $^1$H NMR (400 MHz, CDCl$_3$): δ 9.06 (br s, 1H), 7.51 (dt, J=0.8, 8.1 Hz, 1H), 7.36 (dd, J=7.7, 0.8 Hz, 1H), 6.96 (t, J=7.8 Hz, 1H), 6.76 (d, J=2.3 Hz, 1H), 3.87 (br m, 4H), 2.43 (t, J=5.1 Hz, 4H), 2.28 (s, 3H). MS: exact mass calculated for C$_{14}$H$_{16}$BrN$_3$O, 321.05; m/z found, 322.1 [M+H]$^+$.

The title compound of the following example (44) was prepared according to the general procedure of Scheme 3.

Example 44

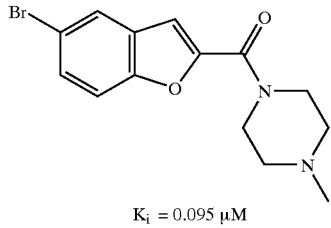

$K_i = 0.095 \, \mu M$ (5-Bromo-benzofuran-2-yl)-(4-methyl-piperazin-1-yl)-methanone 5-Bromo-benzofuran-2-carboxylic acid (0.346 g) in THF (7 mL) was treated with carbonyldiimidazole (0.214 g) and stirred at ambient temperature for 2 h whereupon methyl-piperazine (0.129 g) was added. The mixture was stirred at ambient temperature for 18 h and then concentrated under reduced pressure. The residue was dissolved in dichloromethane and washed with saturated sodium bicarbonate solution, whereupon the organic portion was separated out, dried over sodium sulfate and filtered. The solvent was evaporated, and the residue was purified via silica gel chromatography (5% 2 M ammonina in methanol/dichloromethane) to afford the title compound (0.222 g). $^1$H NMR (400 MHz, CDCl$_3$): δ 7.75 (d, J=1.9 Hz, 1H), 7.45 (dd, J=8.8, 1.9 Hz, 1H), 7.37 (d, J=8.8 Hz, 1H), 3.83 (br s, 4H), 2.48 (t, J=4.8 Hz, 4H), 2.33 (s, 3H). $^{13}$C NMR (400 MHz, CDCl$_3$) δ 159.4, 153.4, 150.3, 129.6, 129.0, 124.9, 116.8, 113.5, 111.3, 55.3, 54.9, 46.8, 46.1, 42.9.

Example 45

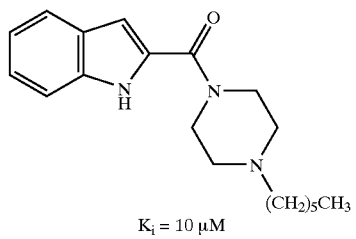

$K_i = 10 \, \mu M$ (4-Hexyl-piperazin-1-yl)-(1H-indol-2-yl)-methanone

Indole-2-carboxylic acid (5.2 g) in THF (200 mL) was treated with carbonyldiimidazole (4.8 g) and stirred at ambient temperature for 10 min whereupon 4-methyl-piperazine-1-carboxylic acid tert-butyl ester (5.0 g) was added. The mixture was stirred at ambient temperature for 72 h and the solvent removed under reduced pressure. The residue was dissolved in ethyl acetate and washed with saturated sodium bicarbonate solution. The organic portion was separated, dried over sodium sulfate and filtered, and solvent was evaporated to afford a solid. Recrystallization from hot ethanol afforded 4-(1H-Indole-2-carbonyl)-piperazine-1-carboxylic acid tert-butyl ester (4.2 g).

4-(1H-Indole-2-carbonyl)-piperazine-1-carboxylic acid tert-butyl ester (0.165 g) in dichloromethane (10 mL) was treated with trifluoroacetic acid (2 mL) and stirred at ambient temperature for 1 h. The solvent was removed under reduced pressure to afford (1H-Indol-2-yl)-piperazin-1-yl-methanone trifluoroacetate salt. ($^1$H NMR (400 MHz, CDCl$_3$): δ 7.63 (d, J=8.07 Hz, 1H), 7.44 (dd, J=8.3, 0.8 Hz, 1H), 7.24 (m, 1H), 7.08 (m, 1H), 6.91 (s, 1H), 4.12 (t, J=5.0 Hz, 4H), 3.35 (t, J=5.3 Hz, 4H)). This intermediate was dissolved in acetone (5 mL), treated with potassium carbonate (0.22 g), iodohexane (0.106 g) and heated at 50° C. for 10 h. Evaporation of the solvent under reduced pressure afforded crude product which was purified via preparative thin layer chromatography eluting with 10% methanol/dichloromethane to give the title compound (0.06 g). $^1$H NMR (400 MHz, CD$_3$OD): δ 7.60 (d, J=8.0 Hz, 1H), 7.42 (d, J=8.3 Hz, 1H), 7.21(ddd, J=8.1, 7.1, 1.1 Hz, 1H), 7.16–7.04 (m, 1H), 6.81 (s, 1H), 3.89 (br s, 4H), 2.56 (t, J=5.0 Hz, 4H), 2.43–2.40 (m, 2H), 1.58–1.52 (m, 2H), 1.34 (br s, 6H), 0.94–0.90 (m, 3H).

The title compounds of the following examples (46–47) were prepared according to the general procedure of Scheme 5, as indicated for Example 74.

Example 46

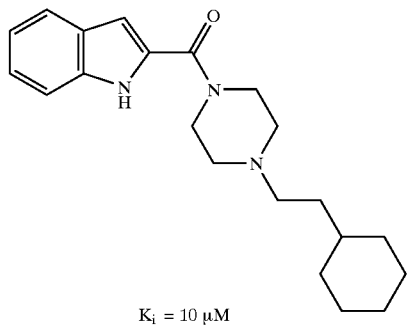

$K_i = 10 \, \mu M$

[4-(2-Cyclohexyl-ethyl)-piperazin-1-yl]-(1H-indol-2-yl)-methanone

Example 47

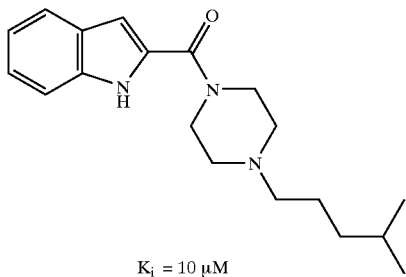

$K_i = 10$ μM

(1H-Indol-2-yl)-[4-(4-methyl-pentyl)-piperazin-1-yl]-methanone

Example 48

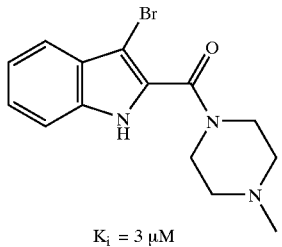

$K_i = 3$ μM

(3-Bromo-1H-indol-2-yl)-(4-methyl-piperazin-1-yl)-methanone (1H-Indol-2-yl)-(4-methyl-piperazin-1-yl)-methanone (Example 4, 0.222 g) in acetic acid (1 mL) at ambient temperature was treated with bromine (0.05 mL) and stirred for 7 h. The reaction mixture was poured into water and adjusted to basic pH by addition of 1 M sodium hydroxide. The mixture was extracted with dichloromethane. The organic extracts were combined, dried over sodium sulfate, filtered, and concentrated to give crude product. Purification via silica gel chromatography, eluting with 1–8% methanol/dichloromethane, afforded the title compound (0.154 g).

Example 49

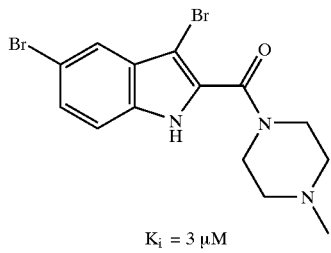

$K_i = 3$ μM

(3,5-Dibromo-1H-indol-2-yl)-(4-methyl-piperazin-1-yl)-methanone (1H-Indol-2-yl)-(4-methyl-piperazin-1-yl)-methanone (Example 4, 0.222 g) in acetic acid (1 mL) at ambient temperature was treated with bromine (0.10 mL) and stirred for 7 h. The reaction mixture was poured into water and adjusted to basic pH by addition of 1 M sodium hydroxide. The mixture was extracted with dichloromethane. The organic extracts were combined, dried over sodium sulfate, filtered, and concentrated to give crude product. Purification via silica gel chromatography, eluting with 1–8% methanol/dichloromethane afforded the title compound (0.123 g).

Example 50

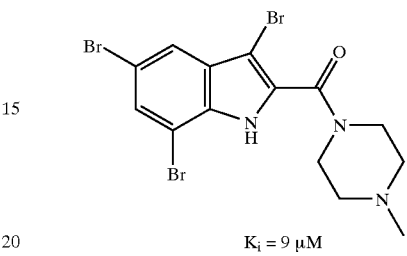

$K_i = 9$ μM

(4-Methyl-piperazin-1-yl)-(3,5,7-tribromo-1H-indol-2-yl)-methanone (1H-Indol-2-yl)-(4-methyl-piperazin-1-yl)-methanone (Example 4, 0.222 g) in acetic acid (1 mL) at ambient temperature was treated with bromine (0.15 mL) and stirred for 7 h. The reaction mixture was poured into water and adjusted to basic pH by addition of 1 M sodium hydroxide. The mixture was extracted with dichloromethane. The organic extracts were combined, dried over sodium sulfate, filtered, and concentrated to give crude product. Purification via silica gel chromatography, eluting with 1–8% methanol/dichloromethane afforded the title compound (0.038 g).

Example 51

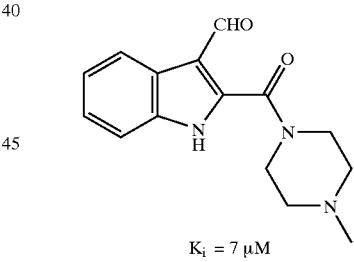

$K_i = 7$ μM

2-(4-Methyl-piperazine-1-carbonyl)-1H-indole-3-carbaldehyde (1H-Indol-2-yl)-(4-methyl-piperazin-1-yl)-methanone (Example 4, 0.206 g) in DMF (1.5 mL) at 0° C. was treated with phosphorus oxychloride (0.1 mL) over 10 min. The reaction mixture was warmed to ambient temperature and stirred for 16 h. The reaction mixture was poured into water and adjusted to neutral pH by addition of 1 M sodium hydroxide. The mixture was extracted with dichloromethane. The organic extracts were combined, dried over sodium sulfate, filtered, and concentrated to give crude product. Purification via silica gel chromatography, eluting with 1–8% methanol/dichloromethane afforded the title compound (0.108 g).

Example 52

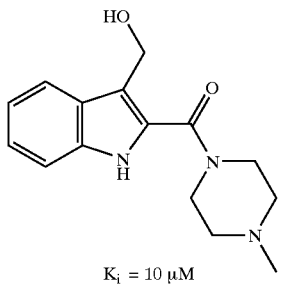

$K_i = 10 \mu M$ (3-Hydroxymethyl-1H-indol-2-yl)-(4-methyl-piperazin-1-yl)-methanone 2-(4-Methyl-piperazine-1-carbonyl)-1H-indole-3-carbaldehyde (Example 51, 0.094 g) in ethyl acetate (1.5 mL) was treated with sodium borohydride (0.024 g) and stirred at ambient temperature for 3 h. The solvent was removed under reduced pressure, and the residue treated with saturated sodium hydrogencarbonate solution and extracted with dichloromethane. The organic extracts were dried over sodium sulfate, filtered, and concentrated. The residue was purified via silica gel chromatography, eluting with 1–8% methanol/dichloromethane, to afford the title compound (0.042 g).

Example 53

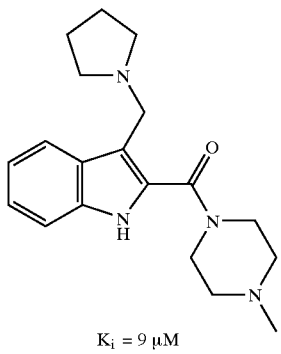

$K_i = 9 \mu M$ (4-Methyl-piperazin-1-yl)-(3-pyrrolidin-1-ylmethyl-1H-indol-2-yl)-methanone (1H-Indol-2-yl)-(4-methyl-piperazin-1-yl)-methanone (Example 4, 0.231 g) in acetic acid (1.5 mL) at ambient temperature was treated with paraformaldehyde (0.4 g) and pyrrolidine (0.16 mL). The reaction mixture was heated at 60° for 6 h then poured into water and the solution adjusted to basic pH by addition of 1 M sodium hydroxide. The mixture was extracted with dichloromethane. The organic extracts were combined, dried over sodium sulfate, filtered, and concentrated to give crude product. Purification via silica gel chromatography, eluting with 1–8% methanol/dichloromethane afforded the title compound (0.1 g).

Example 54

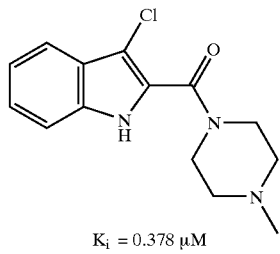

$K_i = 0.378 \mu M$ (3-Chloro-1H-indol-2-yl)-(4-methyl-piperazin-1-yl)-methanone (1H-Indol-2-yl)-(4-methyl-piperazin-1-yl)-methanone (Example 4, 0.5 g) in dichloromethane (3 mL) at ambient temperature was treated with N-chlorosuccinimide (0.301 g) and stirred for 6 h. The reaction mixture was diluted with ether, washed with water, saturated sodium hydrogencarbonate solution and then brine, dried over sodium sulfate, filtered, and concentrated to give crude product. Purification via silica gel chromatography, eluting with 1–8% methanol/dichloromethane, afforded the title compound (0.36 g). $^1$H NMR (400 MHz, CDCl$_3$): δ 2.36 (3H), 2.52 (4H), 3.79 (4H), 7.21 (1H), 7.31 (1H), 7.38 (1H), 7.64 (1H), 9.05 (1H).

Example 55

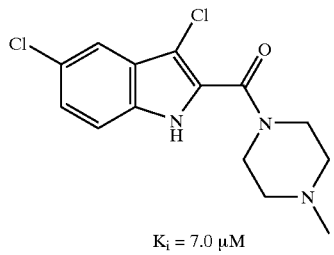

$K_i = 7.0 \mu M$ (3,5-Dichloro-1H-indol-2-yl)-(4-methyl-piperazin-1-yl)-methanone (5-Chloro-1H-indol-2-yl)-(4-methyl-piperazin-1-yl)-methanone (Example 1, 0.23 g) in dichloromethane (3 mL) at ambient temperature was treated with N-chlorosuccinimide (0.123 g) and stirred for 18 h. The reaction mixture was diluted with ether, washed with water, saturated sodium hydrogencarbonate solution and then brine, dried over sodium sulfate, filtered, and concentrated to give crude product. Purification via silica gel chromatography, eluting with 1–8% methanol/dichloromethane afforded the title compound (0.13 g). $^1$H NMR (400 MHz, CDCl$_3$): δ 2.36 (3H), 2.53 (4H), 3.79 (4H), 7.22 (1H), 7.29 (1H), 7.58 (1H), 10.39 (1H).

Example 56

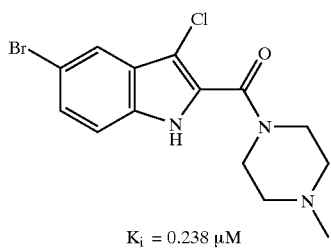

$K_i = 0.238 \mu M$ (5-Bromo-3-chloro-1H-indol-2-yl)-(4-methyl-piperazin-1-yl)-methanone (5-Bromo-1H-indol-2-yl)-(4-methyl-piperazin-1-yl)-methanone (Example 3, 0.27 g) in dichloromethane (3 mL) at ambient temperature was treated with N-chlorosuccinimide (0.103 g) and stirred for 18 h. The reaction mixture was diluted with ether, washed with water, saturated sodium hydrogencarbonate solution and then brine, dried over sodium sulfate, filtered, and concentrated to give crude product. Purification via silica gel chromatography, eluting with 1–8% methanol/dichloromethane afforded the title compound (0.16 g). $^1$H NMR (400 MHz, CDCl$_3$): δ 2.35 (3H), 2.52 (4H), 3.78 (4H), 7.23 (1H), 7.35 (1H), 7.74 (1H), 9.84 (1H).

Example 57

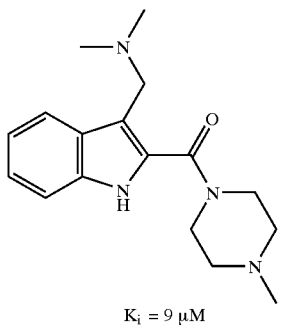

$K_i = 9 \mu M$ (3-Dimethylaminomethyl-1H-indol-2-yl)-(4-methyl-piperazin-1-yl)-methanone The title compound was prepared from (1H-Indol-2-yl)-(4-methyl-piperazin-1-yl)-methanone (Example 4) according to the general procedure of Example 53 (See: J. Am. Chem. Soc., 71:3541, 1949). $^1$H NMR (400 MHz, CDCl$_3$: δ 9.39 (br, 1H), 7.78 (m, 1H), 7.34 (m, 1H), 7.21 (m, 1H), 7.11 (m, 1H), 5.28 (s, 2H), 3.69 (br, 4H), 2.40 (br, 4H), 2.29 (s, 3H), 2.24 (s, 6H)). MS (electrospray): exact mass calculated for C$_{17}$H$_{24}$N$_4$O, 300.20; m/z found, 301.1 [M+H]$^+$.

Example 58

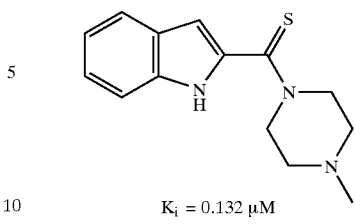

$K_i = 0.132 \mu M$ (1H-Indol-2-yl)-(4-methyl-piperazin-1-yl)-methanethione (1H-Indol-2-yl)-(4-methyl-piperazin-1-yl)-methanone (Example 4, 0.123 g) in THF (1 mL) was treated with Lawesson's reagent (0.243 g) and stirred at ambient temperature overnight. The reaction mixture was concentrated under reduced pressure, and the residue was purified via preparative thin layer chromatography to afford the title compound (0.02 g). $^1$H NMR (400 MHz, CDCl$_3$): δ 9.21 (br s, 1H), 7.62 (d, J=8.0 Hz, 1H), 7.40 (d, J=8.3 Hz, 1H), 7.29 (d, J=7.3 Hz, 1H), 7.12 (m, 1H), 6.60 (s, 1H), 4.39 (br s, 4H), 3.85 (br s, 4H), 2.63 (s, 3H).

The title compounds of the following examples (59 and 60) were prepared according to the general procedure of Scheme 1.

Example 59

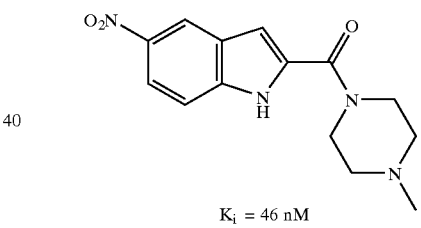

$K_i = 46 nM$ (4-Methyl-piperazin-1-yl)-(5-nitro-1H-indol-2-yl)-methanone

A mixture of 5-nitroindole-2-carboxylic acid (4.38 g) and 1-(3-dimethylaminopropyl)-3-ethylcarbodiimide hydrochloride (EDC, 4.89 g) in dichloromethane (150 mL) was treated with N-methylpiperazine (2.83 mL) and stirred at ambient temperature for 16 h. The reaction mixture was poured into dichloromethane (200 mL), washed with water, saturated sodium hydrogencarbonate solution and then brine, dried over sodium sulfate, filtered, and concentrated under reduced pressure. The residue was purified via silica gel chromatography (0–10% 2 M ammonia in methanol/dichloromethane) to give the title compound (1.8 g). $^1$H NMR (400 MHz, CDCl$_3$): δ 10.97 (br s, 1H), 8.58 (d, J=2.15 Hz, 1H), 8.11 (dd, J=2.15, 7.04 Hz, 1H), 7.44 (d, J=9.00 Hz, 1H), 6.89 (s, 1H), 3.95 (br m, 4H), 2.52 (t, J=4.89 Hz, 4H), 2.34 (s, 3H). MS (electrospray): exact mass calculated for C$_{14}$H$_{16}$N$_4$O$_3$, 288.12; m/z found, 289.1 [M+H]$^+$.

Example 60

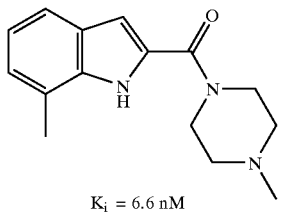

K$_i$ = 6.6 nM (7-Methyl-1H-indol-2-yl)-(4-methyl-piperazin-1-yl)-methanone

A mixture of 7-methylindole-2-carboxylic acid (1.79 g, 10 mmol),1-(3-dimethylaminopropyl)-3-ethylcarbodiimide hydrochloride (EDC, 2.88 g, 15 mmol) in CH$_2$Cl$_2$ (100 mL) was treated with N-methylpiperazine (2.22 mL, 20 mmol). The reaction mixture was stirred at ambient temperature for 16 h and then concentrated under reduced pressure. The residue was dissolved in CH$_2$Cl$_2$ (100 mL), washed with water (25 mL×2) and then brine (25 mL), dried over sodium sulfate, filtered, and concentrated under reduced pressure. This product was purified via silica gel chromatography (5–10% methanol/dichloromethane) to give the title compound as a white solid (2.5 g, 97.3%). $^1$H NMR (400 MHz, CDCl$_3$): δ 11.07 (br s, 1H), 7.43 (d, J=7.04 Hz, 1H), 7.00–6.92 (m, 2H), 6.71 (d, J=1.96 Hz, 1H), 3.86 (br s, 4H), 2.37 (s, 3H), 2.35–2.28 (m, 4H), 2.19 (s, 3H). MS (electrospray): exact mass calculated for C$_{15}$H$_{19}$N$_3$O, 257.15; m/z found, 258.2 [M+H]$^+$.

Example 61

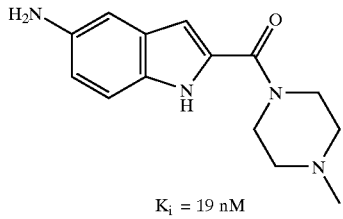

K$_i$ = 19 nM (5-Amino-1H-indol-2-yl)-(4-methyl-piperazin-1-yl)-methanone

The product of Example 59, (4-Methyl-piperazin-1-yl)-(5-nitro-1H-indol-2-yl)-methanone (1.8 g) was dissolved in CH$_3$OH (50 mL). At room temperature, ammonium formate (3.94 g) was added, followed by 10% palladium on carbon (0.66 g). The reaction mixture was heated to reflux for forty min, cooled and filtered through celite pad. The filtrate was concentrated and the residue was purified via silica gel chromatography (3–10% 2 M ammonia in methanol/dichloromethane) to give the title compound (1.60 g). $^1$H NMR (400 MHz, CDCl$_3$): δ 10.46 (br s, 1H), 7.12 (d, J=8.80 Hz, 1H), 6.81 (d, J=2.15 Hz, 1H), 6.64 (dd, J=2.15, 6.46 Hz, 1H), 6.54 (d, J=1.37 Hz, 1H), 3.88 (br m, 4H), 3.70 (br s, 2H), 2.40 (t, J=4.70 Hz, 4H), 2.25 (s, 3H). MS (electrospray): exact mass calculated for C$_{14}$H$_{18}$N$_4$O, 258.15; m/z found, 259.1 [M+H]$^+$.

Example 62

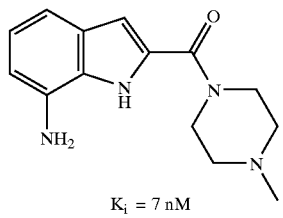

K$_i$ = 7 nM (7-Amino-1H-indol-2-yl)-(4-methyl-piperazin-1-yl)-methanone

The product of Example 8, (4-Methyl-piperazin-1-yl)-(7-nitro-1H-indol-2-yl)-methanone (6.4 g, 22.2 mmol), was dissolved in CH$_3$OH (110 mL). At room temperature, ammonium formate (14.0 g, 222 mmol) was added, followed by 10% palladium on carbon (2.4 g, 2.22 mmol). The reaction mixture was heated to reflux for forty min, cooled, and then filtered through a celite pad. The filtrate was concentrated, and the residue was purified via silica gel chromatography (3–10% 2 M ammonia in methanol/dichloromethane) to give the title compound (4.4 g, 76.7%) as an off-white solid. $^1$H NMR (400 MHz, CDCl$_3$/CD$_3$OD): δ 7.08 (d, J=7.83 Hz, 1H), 6.94 (t, J=7.83 Hz, 1H), 6.73 (s, 1H), 6.58 (d, J=7.63 Hz, 1H), 4.12 (s, 2H), 3.92 (br s, 4H), 2.51 (br s, 4H), 2.34 (s, 3H). MS (electrospray): exact mass calculated for C$_{14}$H$_{18}$N$_4$O, 258.15; m/z found, 259.1 [M+H]$^+$.

The title compounds of the following examples (63 through 66) were prepared according to the general procedure of Scheme 1.

Example 63

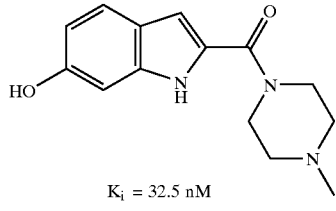

K$_i$ = 32.5 nM (6-Hydroxy-1H-indol-2-yl)-(4-methyl-piperazin-1-yl)-methanone

6-Methoxy-1H-indole-2-carboxylic acid ethyl ester (5.0 g) was treated with lithium hydroxide (2.33 g) in THF (90 mL) followed by water (30 mL) and stirred at ambient temperature for 16 h. The solution was acidified with 10% hydrochloric acid, diluted with water and extracted with ethyl acetate. The organic extracts were washed with brine, dried over sodium sulfate, filtered, and concentrated to afford 6-Methoxy-1H-indole-2-carboxylic acid (4.60 g). This material (4.64 g) and 1-(3-dimethylaminopropyl)-3-ethylcarbodiimide hydrochloride (5.60 g) in dichloromethane (200 mL) were treated with N-methylpiperazine (3.23 mL) and stirred at ambient temperature for 16 h. The reaction mixture was poured into dichloromethane (200 mL), washed with water, saturated sodium hydrogencarbonate solution and then brine, dried over sodium sulfate, filtered, and concentrated under reduced pressure. The residue was purified via silica gel chromatography (0–10% 2 M ammonia in methanol/dichloromethane) to give (6-Methoxy-1H-indol-2-yl)-(4-methyl-piperazin-1-yl)-methanone (6.60 g). This material (0.16 g) was dissolved in dichloromethane (10 mL). At room temperature, 1 M boron tribromide (1.5 mL) was added dropwise. The reaction mixture was heated to reflux overnight, and then cooled, quenched with saturated sodium hydrogencarbonate solution, and extracted with dichloromethane. The organic extracts were washed with brine, dried over sodium sulfate, filtered, and concentrated. The residue was purified via silica gel chromatography (0–10% 2 M ammonia in methanol/dichloromethane) to give the title compound (0.12 g). $^1$H NMR (400 MHz, CDCl$_3$/CD$_3$OD): δ 7.22 (d, J=8.41 Hz, 1H), 6.62 (d, J=2.15 Hz, 1H), 6.5'-6.47 (m, 2H), 3.69 (br s, 4H), 2.30 (t, J=5.09 Hz, 4H), 2.13 (s, 3H). MS (electrospray): exact mass calculated for C$_{14}$H$_{17}$N$_3$O$_2$, 259.13; m/z found, 260.1 [M+H]$^+$.

Example 64

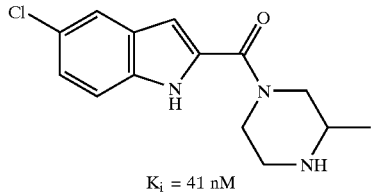

K$_i$ = 41 nM (5-Chloro-1H-indol-2-yl)-(3-methyl-piperazin-1-yl)-methanone

A mixture of 5-chloroindole-2-carboxylic acid (0.196 g) and 1-(3-dimethylaminopropyl)-3-ethylcarbodiimide hydrochloride (0.288 g) in dichloromethane (10 mL) was treated with 2-Methyl-piperazine (0.15 g) and stirred at ambient temperature for 16 h. The reaction mixture was poured into dichloromethane (50 mL), washed with water, saturated sodium hydrogencarbonate solution and then brine, dried over sodium sulfate, filtered and concentrated under reduced pressure. The residue was purified via silica gel chromatography (0–10% methanol/dichloromethane) to give the title compound (0.229 g). $^1$H NMR (400 MHz, CDCl$_3$): δ 10.99 (br s, 1H), 7.55 (d, J=1.76 Hz, 1H), 7.33 (d, J=8.80 Hz, 1H), 7.14 (dd, J=1.96, 6.65 Hz, 1H), 6.63 (br s, 1H), 4.55 (br s, 2H), 3.23–2.61 (m, 5H), 1.76 (br s, 1H), 1.08 (d, J=5.87 Hz, 1H). MS (electrospray): exact mass calculated for C$_{14}$H$_{16}$ClN$_3$O, 277.10; m/z found, 278.1 [M+H]$^+$.

Example 65

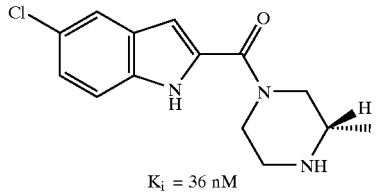

K$_i$ = 36 nM (5-Chloro-1H-indol-2-yl)-(3-methyl-piperazin-1-yl)-methanone $^1$H NMR (400 MHz, CDCl$_3$): δ 10.99 (br s, 1H), 7.55 (d, J=1.76 Hz, 1H), 7.33 (d, J=8.80 Hz, 1H), 7.14 (dd, J=1.96, 6.65 Hz, 1H), 6.63 (br s, 1H), 4.55 (br s, 2H), 3.23–2.61 (m, 5H), 1.76 (br s, 1H), 1.08 (d, J=5.87 Hz, 1H). MS (electrospray): exact mass calculated for C$_{14}$H$_{16}$ClN$_3$O, 277.10; m/z found, 278.1 [M+H]$^+$.

Example 66

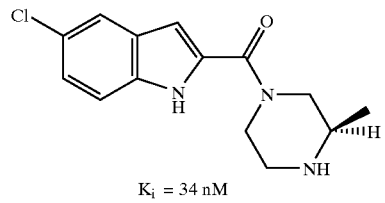

K$_i$ = 34 nM (5-Chloro-1H-indol-2-yl)-(3-methyl-piperazin-1-yl)-methanone $^1$H NMR (400 MHz, CDCl$_3$): δ 10.99 (br s, 1H), 7.55 (d, J=1.76 Hz, 1H), 7.33 (d, J=8.80 Hz, 1H), 7.14 (dd, J=1.96, 6.65 Hz, 1H), 6.63 (br s, 1H), 4.55 (br s, 2H), 3.23–2.61 (m, 5H), 1.76 (br s, 1H), 1.08 (d, J=5.87 Hz, 1H). MS (electrospray): exact mass calculated for C$_{14}$H$_{16}$ClN$_3$O, 277.10; m/z found, 278.1 [M+H]$^+$.

Example 67

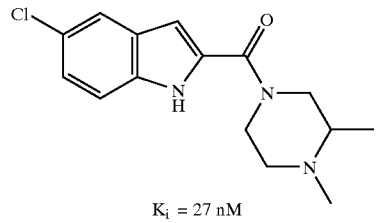

K$_i$ = 27 nM (5-Chloro-1H-indol-2-yl)-(3,4-dimethyl-piperazin-1-yl)-methanone

The product of Example 64, (5-Chloro-1H-indol-2-yl)-(3-methyl-piperazin-1-yl)-methanone (0.19 g) was dissolved in dichloromethane (10 mL). At room temperature, paraformaldehyde (0.031 g) was added, followed by acetic acid (1 drop). The reaction mixture was stirred at ambient temperature for 5 h. Sodium triacetoxybrohydride (0.318 g) was added. The reaction mixture was stirred at ambient temperature for 16 h and poured into dichloromethane (20 mL), washed with water, saturated sodium hydrogencarbonate solution and then brine, dried over sodium sulfate, filtered, and concentrated under reduced pressure. The residue was purified via silica gel chromatography (0–10% methanol/dichloromethane) to give the title compound (0.22 g). $^1$H NMR (400 MHz, CDCl$_3$): δ 10.69 (br s, 1H), 7.56 (d, J=1.76 Hz, 1H), 7.33 (d, J=8.80 Hz, 1H), 7.16 (dd, J=1.96, 6.66 (d, J=1.57 Hz, 1H), 4.63–4.36 (m, 2H), 3.63–2.67 (m, 3H), 2.30 (s, 3H), 2.30–2.20 (m, 1H), 2.18–2.09 (m, 1H), 1.12 (d, J=5.87 Hz, 1H). MS (electrospray): exact mass calculated for C$_{15}$H$_{18}$ClN$_3$O, 291.11; m/z found, 292.1 [M+H]$^+$.

The title compound of the following example (68) was prepared according to the general procedure of Scheme 5.

Example 68

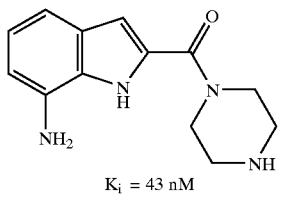

K$_i$ = 43 nM (7-Amino-1H-indol-2-yl)-piperazin-1-yl-methanone

A mixture of 7-nitroindole-2-carboxylic acid (4.38 g) and 1-(3-dimethylaminopropyl)-3-ethylcarbodiimide hydrochloride (4.89 g) in dichloromethane (50 mL) was treated with piperazine-1-carboxylic acid tert-butyl ester (1.63 g) and stirred at ambient temperature for 16 h. The reaction mixture was poured into in dichloromethane (20 mL), washed with water, saturated sodium hydrogencarbonate solution and then brine, dried over sodium sulfate, filtered, and concentrated under reduced pressure. The residue was purified via silica gel chromatography (0–5% methanol/dichloromethane) to give 4-(7-Nitro-1H-indole-2-carbonyl)-piperazine-1-carboxylic acid tert-butyl ester (2.17 g). This material (1.69 g) was dissolved in CH$_3$OH (50 mL). At room temperature, ammonium formate (2.85 g) was added, followed by 10% palladium on carbon (0.47 g). The reaction mixture was heated to reflux for forty min, cooled and filtered through celite pad. The filtrate was concentrated and the residue was purified via silica gel chromatography (0–10% methanol/dichloromethane) to give 4-(7-Amino-1H-indole-2-carbonyl)-piperazine-1-carboxylic acid tert-butyl ester (1.34 g). This material (1.3 g) was treated with 20% trifluoroacetic acid/dichloromethane (50 mL) and stirred at ambient temperature for 1 h. The solvent was removed under reduced pressure to afford (7-Amino-1H-indol-2-yl)-piperazin-1-yl-methanone trifluoroacetate salt. This intermediate was dissolved in dichloromethane (100 mL), washed with saturated sodium hydrogencarbonate solution and then brine, dried over sodium sulfate, filtered, and concentrated under reduced pressure. The residue was purified via silica gel chromatography (0–10% 2M ammonia in methanol/dichloromethane) to give the title compound (0.824 g). $^1$H NMR (400 MHz, CDCl$_3$/CD$_3$OD): δ 7.09 (d, J=7.83 Hz, 1H), 6.95 (t, J=7.63 Hz, 1H), 6.72 (s, 1H), 6.60 (d, J=7.63 Hz, 1H), 4.20 (br s, 4H), 3.88 (br s, 4H), 2.94 (t, J=5.09 Hz, 3H). MS (electrospray): exact mass calculated for C$_{13}$H$_{16}$N$_4$O, 244.13; m/z found, 245.1 [M+H]$^+$.

The title compounds of the following examples (69–70) were prepared according to the general procedure of Scheme 4.

Example 69

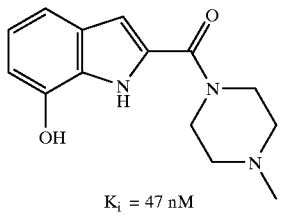

K$_i$ = 47 nM (7-Hydroxy-1H-indol-2-yl)-(4-methyl-piperazin-1-yl)-methanone

At room temperature, diethyl oxalate (13.6 mL) was added to a solution of potassium ethoxide (8.4 g) in anhydrous ethyl ether (200 mL). After 10 min, 3-methyl-2-nitroanisole (16.7 g) was added and stirred at ambient temperature for 24 h. The lumpy, deep purple potassium salt was separated by filtration and washed with anhydrous ether until the filtrate remained colorless. This salt was dissolved in aqueous ammonium chloride, and the solution was extracted with dichloromethane. The combined organic extracts were washed with brine, dried over sodium sulfate and filtered, and the solvent was evaporated. The residue was purified via silica gel chromatography (5–30% ethyl acetate/hexanes) to give 3-(3-Methoxy-2-nitro-phenyl)-2-oxo-propionic acid ethyl ester (14.0 g). This material (14.0 g) was dissolved in ethanol (200 mL) containing 5 wt. % palladium on activated carbon (1.4 g) and placed on a Parr hydrogenator at 60 psi H$_2$. After 2 h, the mixture was filtered through Celite, and concentrated to give a clear liquid. The liquid was purified by silica gel chromatography (5%-30% EtOAc/Hexanes) to obtain (7-Methoxy-1H-indol-2-yl)-(4-methyl-6-Methoxy-1H-indole-2-carboxylic acid ethyl ester (11.7 g). This ethyl ester (4.0 g) was treated with lithium hydroxide (1.75 g) in THF (100 mL) followed by water (30 mL) and stirred at ambient temperature for 16 h. The solution was acidified with 10% hydrochloric acid, diluted with water and extracted with ethyl acetate. The organic extracts were washed with brine, dried over sodium sulfate, filtered, and concentrated to afford 6-Methoxy-1H-indole-2-carboxylic acid (3.50 g). This material (3.50 g) and 1-(3-dimethylaminopropyl)-3-ethylcarbodiimide hydrochloride (5.26 g) in dichloromethane (100 mL) were treated with N-methylpiperazine (3.05 mL) and stirred at ambient temperature for 16 h. The reaction mixture was poured into dichloromethane (200 mL), washed with water, saturated sodium hydrogencarbonate solution and then brine, dried over sodium sulfate, filtered, and concentrated under reduced pressure. The residue was purified via silica gel chromatography (0–10% methanol/dichloromethane) to give (7-Methoxy-1H-indol-2-yl)-(4-methyl-piperazin-1-yl)-methanone (4.50 g). This material (3.5 g) was dissolved in dichloromethane (85 mL). At room temperature, 1 M Boron tribromide (2.42 mL) was added dropwise. The reaction mixture was heated to reflux for 2 h, cooled, and then quenched with saturated sodium hydrogencarbonate solution. The suspension was filtered. The filtrate was washed with saturated sodium hydrogencarbonate solution and then brine, dried over sodium sulfate and filtered, and solvent was evaporated. The residue was purified via silica gel chromatography (0–10% methanol/dichloromethane) to give the title compound (1.95 g). $^1$H NMR (400 MHz, CDCl$_3$/CD$_3$OD): δ 7.52 (s, 1H), 7.16 (dd, J=0.78, 7.24 Hz, 1H), 6.96 (t, J=7.63 Hz, 1H), 6.77 (s, 1H), 6.70 (dd, J=0.98, 6.65 Hz, 1H), 3.93 (br s, 4H), 2.55 (t, J=5.09 Hz, 4H), 2.38 (s, 3H). MS (electrospray): exact mass calculated for C$_{14}$H$_{17}$N$_3$O$_2$, 259.13; m/z found, 260.1 [M+H]$^+$.

Example 70

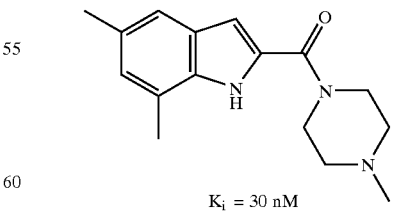

K$_i$ = 30 nM (5,7-Dimethyl-1H-indol-2-yl)-(4-methyl-piperazin-1-yl)-methanone $^1$H NMR (400 MHz, CDCl$_3$): δ 10.68 (br s, 1H), 7.20 (s, 1H), 6.80 (s, 1H), 6.65 (d, J=2.15 Hz, 1H), 3.91 (br s, 4H), 2.39 (t, J=4.50 Hz, 4H), 2.35 (s, 6H), 2.26 (s, 3H). MS (electrospray): exact mass calculated for $C_{16}H_{21}N_3O$, 271.17; m/z found, 272.1 $[M+H]^+$.

Example 71

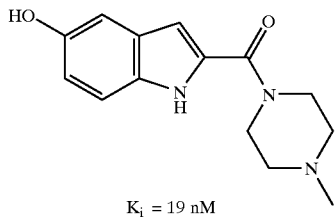

$K_i = 19$ nM (5-Hydroxy-1H-indol-2-yl)-(4-methyl-piperazin-1-yl)-methanone

A mixture of the product of Example 5, (5-Benzyloxy-1H-indol-2-yl)-(4-methyl-piperazin-1-yl)-methanone (0.2 g) in a mixture of ethanol (3 mL) and ethylacetate (5 mL) was treated with 10% palladium on carbon (approximately 0.025 g) and hydrogenated at atmospheric pressure for 2 h. The reaction mixture was filtered through a pad of Celite and the residue washed with methanol. The solvent in the combined filtrates was removed under reduced pressure, and the residue was purified via silica gel chromatography (3–10% 2 M ammonia in methanol/dichloromethane) to afford the title compound (0.034 g, 23%). $^1$H NMR (400 MHz, CD$_3$OD): δ 7.20 (d, J=8.0 Hz, 1H), 6.90 (m, 1H), 6.75 (dd, J=4, 8 Hz, 1H), 6.54 (m,1H), 3.80 (br.m, 4H), 2.44 (m, 4H), 2.27 (s, 3H). MS (electrospray): exact mass calculated for $C_{14}H_{17}N_3O_2$, 259.13; m/z found, 260.0 $[M+H]^+$.

Example 72

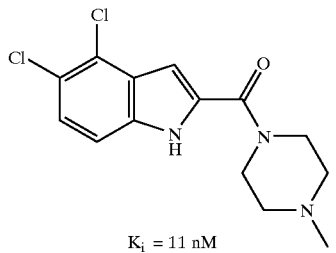

$K_i = 11$ nM (4,5-Dichloro-1H-indol-2-yl)-(4-methyl-piperazin-1-yl)-methanone

The title compound was prepared according to the general procedure of Scheme 2. A mixture of 3,4-dichlorophenylhydrazine (5.0 g) in benzene (50 mL) was treated sequentially with ethylpyruvate (2.6 mL) and p-toluenesulfonic acid (trace). The mixture was heated at reflux temperature (Dean and Stark conditions) for 5 h then cooled to ambient temperature to afford a solution of 2-[(3,4-dichloro-phenyl)-hydrazono]-propionic acid ethyl ester. Separately a solution of p-toluenesulfonic acid (15 g) in benzene (150 mL) was heated at reflux temperature (Dean and Stark conditions) for 2 h and then treated with the hydrazone solution. After 3 h the reaction mixture was cooled, treated with saturated sodium hydrogen carbonate solution and diethyl ether. The organic fraction was separated, washed with saturated sodium hydrogen carbonate solution and then brine, dried over magnesium sulfate and filtered, and solvent was evaporated to give an orange solid. The solid was purified via silica gel chromatography (15–75% ethylacetate/hexane) to afford 4,5-Dichloro-1H-indole-2-carboxylic acid ethyl ester (0.5 g, 8%) and 5,6-Dichloro-1H-indole-2-carboxylic acid ethyl ester (0.297 g, 5%). These materials were used separately without further purification.

4,5-Dichloro-1H-indole-2-carboxylic acid ethyl ester (0.5 g) was treated with 1 M lithium hydroxide in ethanol (3 mL) and heated, water bath, for 2 h. The solution was acidified with 10% hydrochloric acid, diluted with water and extracted with ethylacetate. The organic extracts were combined, dried over sodium sulfate and filtered, and solvent was evaporated to give 4,5-dichloro-1H-indole-2-carboxylic acid (0.27 g, 60%). This material was treated with -ethyl-3-(3'-dimethylaminopropyl)-carbodiimide hydrochloride (0.5 g), HOBT (0.4 g) and N,N-diisopropylethylamine (1 mL) in DMF (2 mL) and dichloromethane (2 mL) was treated with N-methylpiperazine (0.2 mL) stirred at ambient temperature for 18 h then diluted with water. The organic portion was separated, washed with brine, dried over sodium sulfate, and filtered. Solvent was removed under reduced pressure, and the residue was purified via silica gel chromatography (3–8% 2 M ammonia in methanol/dichloromethane) to give the title compound (0.15 g, 40%). $^1$H NMR (400 MHz, CDCl$_3$): δ 10.2 (br.s, 1H), 7.25–7.16 (m, 2H), 6.75 (d, J=2 Hz, 1H), 3.92 (br.m, 4H), 2.47 (m, 4H), 2.30 (s, 3H). MS (electrospray): exact mass calculated for $C_{14}H_{15}Cl_2N_3O$, 311.06; m/z found, 312.0 $[M+H]^+$.

Example 73

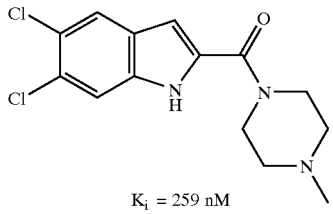

$K_i = 259$ nM (5,6-Dichloro-1H-indol-2-yl)-(4-methyl-piperazin-1-yl)-methanone

Using the procedure of the previous example (72), the title compound was prepared from 5,6-Dichloro-1H-indole-2-carboxylic acid ethyl ester. $^1$H NMR (400 MHz, CDCl$_3$): δ 9.9 (br.s, 1H), 7.97 (s, 1H), 7.79 (m, 1H), 6.94 (m, 1H), 4.20 (br.m, 4H), 2.77 (m, 4H), 2.26 (s, 3H). MS (electrospray): exact mass calculated for $C_{14}H_{15}Cl_2N_3O$, 311.06; m/z found, 312.0 $[M+H]^+$.

The title compound of the following example (74) was prepared according to the general procedure of Scheme 5.

Example 74

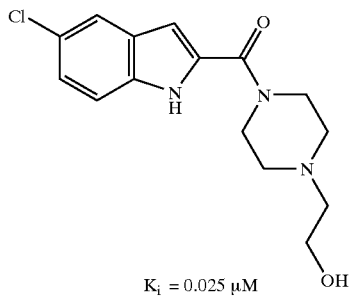

$K_i$ = 0.025 µM (5-Chloro-1H-indol-2-yl)-[4-(2-hydroxy-ethyl)-piperazin-1-yl]-methanone A. 4-(5-Chloro-1H-indole-2-carbonyl)-piperazine-1-carboxylic Acid tert-butyl ester A mixture of 5-chloroindole-2-carboxylic acid (10 g), tert-butyl 1-piperazinecarboxylate (10.5 g) and 4-dimethylaminopyridine (6.3 g) in $CH_2Cl_2$ (200 mL) was treated with a catalytic amount of HOBT (0.2 g). The resulting mixture was cooled to 0° C., and EDCl (10.8 g) was added. The reaction was then slowly warmed to ambient temperature and stirred for 24 h then concentrated under reduced pressure. Water was added to the resulting residue. The product precipitated and was washed with water (2×50 mL) and $Et_2O$ (30 mL). The resulting solid was dried under reduced pressure to yield (18.2 g). MS (electrospray): exact mass calculated for $C_{18}H_{22}ClN_3O_3$, 363.13; m/z found, 362.3 [M−H]⁻.

B. (5-Chloro-1H-indol-2-yl)-piperazin-1-yl-methanone

The product from Step A (11 g) was suspended in $CH_2Cl_2$ (75 mL), and TFA was added dropwise (75 mL). The resulting solution was stirred overnight at ambient temperature. The reaction solution was concentrated under reduced pressure, and the resulting residue was dissolved in $CH_2Cl_2$ (100 mL). Saturated aqueous $NaHCO_3$ (100 mL) was added slowly with stirring. After 20 min the organic layer was separated, washed with water (10 mL) and then brine (30 mL), and dried over $Na_2SO_4$. The organic layer was then concentrated under reduced pressure and purified via silica gel chromatography (0–35% methanol/dichloromethane) to give the title compound (7.6 g). MS (electrospray): exact mass calculated for $C_{13}H_{14}ClN_3O$, 263.08; m/z found, 264.1 [M+H]⁺.

C. (5-Chloro-1H-indol-2-yl)-[4-(2-hydroxy-ethyl)-piperazin-1-yl]-methanone

The product from Step B (1.0 g) was dissolved in $CH_3CN$ (10 mL) and treated with 2-bromoethanol (0.5 g) and then $K_2CO_3$ (0.8 g). The resulting mixture was heated at 60° C. overnight. The mixture was cooled to ambient temperature, filtered, and concentrated under reduced pressure. The resulting residue was purified via silica gel chromatography (0–10% methanol/dichloromethane) to give the title compound (0.5 g). ¹H NMR (400 MHz, CDCl₃): δ 10.09 (br s, 1H), 7.61 (d, J=2.0 Hz, 1H), 7.37 (d, J=8.8 Hz, 1H), 7.23 (dd, J=2.0, 8.8 Hz, 1H), 6.69 (d, J=0.8 Hz, 1H), 3.95 (br m, 3H), 3.72–3.69 (m, 2H), 2.67–2.64 (m, 4H), 2.52 (br s, 3H). MS (electrospray): exact mass calculated for $C_{15}H_{18}ClN_3O_2$, 307.78; m/z found, 308.1 [M+H]⁺.

Example 75

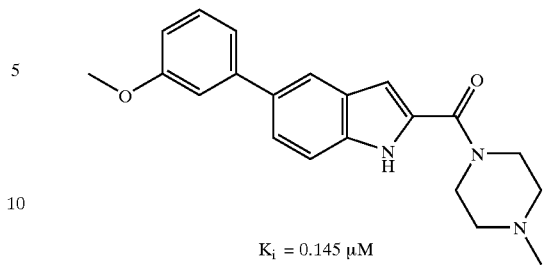

$K_i$ = 0.145 µM

[5-(3-Methoxy-phenyl)-1H-indol-2-yl]-(4-methyl-piperazin-1-yl)-methanone

A suspension of (5-Bromo-1H-indol-2-yl)-(4-methyl-piperazin-1-yl)-methanone (Example 3, 0.057 g) in dry toluene (0.5 mL) was treated with $Pd(OH)_2$ (0.001 g) under $N_2$ atmosphere. The resulting mixture was then treated with 3-methoxyphenylboronic acid (0.057 g) and then $K_3PO_4$ (0.12 g), and heated at 95° C. for 24 h. The reaction mixture was cooled to ambient temperature and diluted with water (2 mL) and toluene (10 mL). The organic layer was separated and washed with brine (2 mL), dried over $Na_2SO_4$, filtered, and concentrated under reduced pressure. The resulting residue was purified via silica gel chromatography (0–12% methanol/dichloromethane) to give the title compound (0.005 g). ¹H NMR (400 MHz, CDCl₃): δ 9.96 (br s, 1H), 7.53 (d, J=1.6 Hz, 1H), 7.51 (d, J=1.6 Hz, 1H), 7.35 (t, J=7.9 Hz, 1H), 7.23 (s, 1H), 7.21 (s, 1H), 7.17 (m, 1H), 6.87 (dd, J=2.2, 8.1 Hz, 1H), 6.82 (d, J=1.8 Hz, 1H), 3.99 (br s, 4H), 3.86 (s, 3H), 2.52 (t, J=4.9 Hz, 4H), 2.35 (s, 3H). MS (electrospray): exact mass calculated for $C_{21}H_{23}N_3O_2$, 349.18; m/z found, 350.2 [M+H]⁺.

The title compound of the following example (76) was prepared according to the general procedure of Example 75.

Example 76

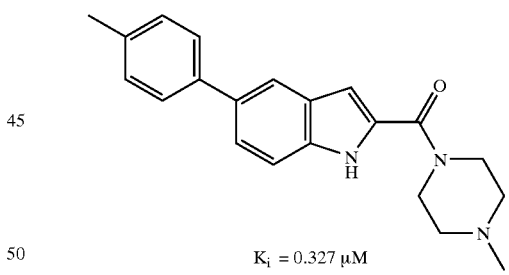

$K_i$ = 0.327 µM (4-Methyl-piperazin-1-yl)-(5-p-tolyl-1H-indol-2-yl)-methanone

¹H NMR (400 MHz, CDCl₃): δ 9.24 (br s, 1H), 7.81 (m, 1H), 7.54–7.46 (m, 5H), 7.26 (d, J=7.8 Hz, 1H), 6.82 (dd, J=0.7, 2.1 Hz, 1H), 3.97 (br s, 4H), 2.52 (t, J=5.1, 4H) 2.40 (s, 3H), 2.36 (s, 3H). MS (electrospray): exact mass calculated for $C_{21}H_{23}N_3O$, 333.18; m/z found, 334.2 [M+H]⁺.

F. BIOLOGICAL EXAMPLES

Example 1

Binding Assay on Recombinant Human Histamine $H_4$ Receptor

SK-N-MC cells or COS7 cells were transiently transfected with pH4R and grown in 150 cm² tissue culture dishes. Cells were washed with saline solution, scraped with a cell scraper and collected by centrifugation (1000 rpm, 5 min). Cell membranes were prepared by homogenization of the cell pellet in 20 mM Tris-HCl with a polytron tissue homogenizer for 10 s at high speed. Homogenate was centrifuged at 1000 rpm for 5 min at 4° C. The supernatant was then collected and centrifuged at 20,000×g for 25 min at 4° C. The final pellet was resuspended in 50 mM Tris-HCl. Cell membranes were incubated with $^3$H-histamine (5 nM–70 nM) in the presence or absence of excess histamine (10000 nM). Incubation occurred at room temperature for 45 min. Membranes were harvested by rapid filtration over Whatman GF/C filters and washed 4 times with ice cold 50 mM Tris HCl. Filters were then dried, mixed with scintillant and counted for radioactivity. SK-N-MC or COS7 cells expressing human histamine $H_4$ receptor were used to measure the affinity of binding of other compounds and their ability to displace $^3$H-ligand binding by incubating the above described reaction in the presence of various concentrations of inhibitor or compound to be tested. For competition binding studies using $^3$H-histamine, $K_i$ values were calculated based on an experimentally determined $K_D$ value of 5 nM and a ligand concentration of 5 nM according to Cheng and Prusoff where; $K_I=(IC_{50})/(1+([L]/(K_D))$.

Example 2

The Inhibition of Zymosan Induced Peritonitis in Mice by Histamine H4 Receptor Antagonists This example demonstrates the discovery that histamine $H_4$ receptor antagonists can block the peritonitis induced by zymosan, which is the insoluble polysaccharide component on the cell wall of *Saccharomyces cerevisiae*. This is commonly used to induce peritonitis in mice and appears to act in a mast cell dependent manner.

Materials and Methods

Animals

Male out-bred Swiss albino mice were purchased from Bantin and Kingman (T.O. strain; Hull, Humberside) and maintained on a standard chow pellet diet with tap water ad libitum and a 12:00 h light/dark cycle. All animals were housed for at least 3 days prior to experimentation to allow body weight to reach ~30 g on the day of the experiment. For this particular experiment body weight was 30.5±0.3 g (n=32). Animals were briefly (30–60 s) anesthetized with halothane for all s.c. and i.p. treatments described below.

Drug Treatment and Experimental Design

Drugs were stored at room temperature, in the dark. On the day of the experiment, drugs were dissolved in sterile PBS as depicted below, and generously vortexed.

The compound from Chemical Example 1 was prepared at 10 mg/5 mL, and injected at 5 mL/kg. Imetit was prepared at 5 mg/5 mL, and injected at 5 mL/kg.

Thioperamide was prepared at 5 mg/5 mL, and injected at 5 mL/kg.

Time −15 min: Compounds or PBS administered s.c. at the reported doses.

Time 0: At time 0, mice received 1 mg zymosan A (Sigma) i.p.

Time +2 h: Compounds or PBS administered s.c. at the reported doses.

Time +4: Peritoneal cavities were washed 4 h later with 3 mL of PBS containing 3 mM EDTA, and the number of migrated leukocytes determined, by taking an aliquot (100 μL) of the lavage fluid and diluting 1:10 in Turk's solution (0.01% crystal violet in 3% acetic acid). The samples were then vortexed and 10 μL of the stained cell solution were placed in a Neubauer haemocytometer. Differential cell counts were performed using a light microscope (Olympus B061). In view of their chromatic characteristics and their nucleus and cytoplasm appearance, polymorphonuclear leukocytes (PMN; >95% neutrophils) could be easily identified.

Experimental groups are described below:

PBS+zymosan, n=8

Compound from Example 1+zymosan, n=8

Imetit+zymosan, n=8

Thioperamide+zymosan, n=8

Statistics

Data are shown for single mice, and also shown as mean±SD or Standard Error (SE) of 8 mice per group. The % of inhibition is also shown. Statistical differences were determined by Anova followed by Bonferroni's post-hoc test.

Results

TABLE 1

Effect of compounds on zymosan peritonitis

| Treatment | n | PMN (10⁶ per mouse) | mean | SD | SE | P value (% inhib) |
|---|---|---|---|---|---|---|
| PBS | 1 | 15.9 | 17.2 | 2.4 | 0.8 | |
| (s.c.) | 2 | 18.3 | | | | |
| | 3 | 16.2 | | | | |
| | 4 | 17.4 | | | | |
| | 5 | 19.8 | | | | |
| | 6 | 12.6 | | | | |
| | 7 | 19.8 | | | | |
| | 8 | 17.7 | | | | |
| Compound 1 | 1 | 9.9 | 6.6 | 2.7 | 1.0 | 0.001 |
| (10 mg/kg; s.c.) | 2 | 3.6 | | | | (−62%) |
| | 3 | 9.3 | | | | |
| | 4 | 3.3 | | | | |
| | 5 | 8.1 | | | | |
| | 6 | 5.1 | | | | |
| | 7 | 6.9 | | | | |
| Imetit | 1 | 19.8 | 17.3 | 2.6 | 0.9 | n.s. |
| (5 mg/kg; s.c.) | 2 | 17.1 | | | | — |
| | 3 | 14.1 | | | | |
| | 4 | 15.3 | | | | |
| | 5 | 21.3 | | | | |
| | 6 | 17.7 | | | | |
| | 7 | 14.1 | | | | |
| | 8 | 18.6 | | | | |
| Thioperamide | 1 | 9.3 | 9.3 | 3.4 | 1.2 | 0.001 |
| (5 mg/kg; s.c.) | 2 | 16.5 | | | | (−46%) |
| | 3 | 7.2 | | | | |
| | 4 | 10.8 | | | | |
| | 5 | 5.4 | | | | |
| | 6 | 9.9 | | | | |
| | 7 | 6.9 | | | | |
| | 8 | 8.1 | | | | |

From data analysis it can be seen that zymosan produced a leukocyte extravasation response that was intense at the 4 h time-point. Treatment with 10 mg/kg Compound 1 significantly reduced PMN influx (compare PBS group to Compound 1 group in Table 1). The degree of inhibition was >60%. Imetit (5 mg/kg) was inactive, whereas a significant inhibitory effect was attained by 5 mg/kg thioperamide.

Conclusion

To conclude, this study demonstrates that a histamine $H_4$ receptor antagonist, Compound 1, given at the dose of 10 mg/kg, is effective in reducing PMN accumulation in an experimental model of cell recruitment in response to local application of zymosan in the mouse peritoneal cavity.

Furthermore thioperamide which is a dual $H_3/H_4$ receptor antagonist is also effective. The dual $H_3/H_4$ receptor agonist, Imetit, does not have any effect. This shows that an antagonist of the histamine $H_4$ receptor can block inflammation induced by zymosan.

Example 3
The Inhibition of Sodium Urate Crystal Induced Peritonitis in Mice by Histamine $H_4$ Receptor Antagonists This example demonstrates the discovery for the first time that histamine $H_4$ receptor antagonists can block the peritonitis induced by sodium urate crystals. Such crystals are the primary cause of the inflammation associated with acute gouty arthritis.

Materials and Methods
Animals

Male out-bred Swiss albino mice were purchased from Bantin and Kingman (T.O. strain; Hull, Humberside) and maintained on a standard chow pellet diet with tap water ad libitum and a 12:00 h light/dark cycle. All animals were housed for at least 3 days prior to experimentation to allow body weight to reach ~30 g on the day of the experiment. For this particular experiment body weight was 30±1 (n=32).

Drug Treatment and Experimental Design

Compound 1 was stored at room temperature in the dark. On the day of the experiment, Compound 1 was dissolved in phosphate buffered saline (PBS) to a concentration of 3 mg/mL. At time −15 min Compound 1 was administered s.c. at the dose of 10 mg/kg, whereas the control group received the vehicle alone (10 mL/kg). Mice received 3 mg mono sodium urate crystals (MSU) given intra-peritoneally at time 0. At time +2 h and time +4 h, Compound 1 (10 mg/kg) or vehicle (10 mL/kg) were given s.c.

Time +6 h: Peritoneal cavities were washed 6 h later with 3 mL of PBS containing 3 mM EDTA, and the number of migrated leukocytes determined, by taking an aliquot (100 µL) of the lavage fluid and diluting 1:10 in Turk's solution (0.01% crystal violet in 3% acetic acid). The samples were then vortexed and 10 µL of the stained cell solution were placed in a Neubauer hematocytometer. Differential cell counts were performed using a light microscope (Olympus B061). In view of their chromatic characteristics and their nucleus and cytoplasm appearance, cells polymorphonuclear cells (PMN, >95% neutrophils) could be easily differentiated Experimental groups are described below:

Vehicle+MSU crystals n=8

Compound 1+MSU crystals n=8

Statistics

Data are shown for single mice, and also shown as mean±SE of (n) mice per group. Statistical differences were determined by Student's t test. A P value <0.05 was taken as significant.

Results

TABLE 2

Effect of Compound 1 on MSU-induced leukocyte migration as evaluated at the 6 h time-point.

| Treatment | n | PMN (10⁶ per mouse) | mean | SD | SE | P value (% inhib) |
|---|---|---|---|---|---|---|
| PBS (s.c.) | 1 | 9.6 | 8.9 | 2.2 | 0.8 | |
| | 2 | 12.9 | | | | |
| | 3 | 7.2 | | | | |
| | 4 | 9.9 | | | | |
| | 5 | 6.6 | | | | |
| | 6 | 7.2 | | | | |
| | 7 | 10.5 | | | | |
| | 8 | 7.5 | | | | |
| Compound 1 (10 mg/kg; s.c.) | 1 | 7.8 | 6.8 | 2.1 | 0.7 | 0.04 (−24%) |
| | 2 | 4.5 | | | | |
| | 3 | 3.0 | | | | |
| | 4 | 7.8 | | | | |
| | 5 | 8.1 | | | | |
| | 6 | 9.3 | | | | |
| | 7 | 6.6 | | | | |
| | 8 | 7.2 | | | | |

Mice were treated with either PBS (10 mL/kg) or Compound 1 (10 mg/kg) at −15 min, +2 H and +4 h, and with 3 mg MSU crystals at time 0. PMN influx into the peritoneal cavity was measured at the 6 h time-point after collection of the lavage fluids and specific staining as described in the experimental section.

Conclusion

As expected, MSU crystals produced a PMN extravasation that was intense at the 6 h time-point. Treatment with a specific histamine $H_4$ receptor antagonist, Compound 1, significantly reduced PMN migration (Table 2): the degree of inhibition was 24%. To Conclude, this study demonstrates that a histamine $H_4$ receptor antagonist is effective in reducing PMN accumulation in an experimental model of cell recruitment in response to local application of MSU crystals in the mouse peritoneal cavity.

Example 4
The Inhibition of Croton Oil Induced Topical Inflammation in Mice by Histamine $H_4$ Receptor Antagonists This example demonstrates the discovery that histamine $H_4$ receptor antagonists can block the inflammation associated with topical application of croton oil.

Materials and Methods
Animals

Male or female ICR derived mice weighing 22±1 g were used. Space allocation for 5 animals was 45×23×15 cm. Mice were house in APEC R cages. All animals were maintained in a controlled temperature (22° C.–24° C.) and humidity (60%–80%) environment with 12 h light/dark cycles. Free access to standard lab chow for Mice (LabDiet Rodent Diet, PMI Nutrition International, USA) and tap water was granted.

Chemicals

Acetone (Wako, Japan), Croton oil (Sigma, USA), Indomethacin (Sigma, USA) and Pyrogen free saline (Astar, Taiwan).

Protocol Croton Oil Induced Topical Inflammation

Groups of 5 ICR derived male mice weighing 22±1 g were used. Compound 1 (10 mg/kg) and vehicle (0.9% NaCl) as well as the positive control Indomethacin (30 mg/kg) were administered subcutaneously to test animals at 30 min before, and 2 and 4 h after croton oil (8% in 20 µL acetone) was applied topically. Ear swelling was measured by Dyer model micrometer gauge 6 h after croton oil as an index of inflammation.

Results

TABLE 3

Effect of Compound 1 on Croton Oil Induced Topical Inflammation

| Treatment | n | Difference in ear Thickness (×0.01 mm) | Mean | SE | P value (% inhib) |
|---|---|---|---|---|---|
| PBS | 1 | 12 | 16.6 | 1.4 | |
| (s.c.) | 2 | 17 | | | |
| | 3 | 15 | | | |
| | 4 | 19 | | | |
| | 5 | 20 | | | |
| Compound 1 | 1 | 12 | 12.0 | 1.2 | 0.03 |
| (10 mg/kg; s.c.) | 2 | 10 | | | (−28%) |
| | 3 | 13 | | | |
| | 4 | 9 | | | |
| | 5 | 16 | | | |
| Indomethacin | 1 | 5 | 10.0 | 1.3 | 0.001 |
| (30 mg/kg; s.c.) | 2 | 10 | | | (−40%) |
| | 3 | 12 | | | |
| | 4 | 12 | | | |
| | 5 | 11 | | | |

Conclusions

In the croton oil induced topical inflammation ear swelling assay, a histamine $H_4$ receptor antagonist, Compound 1, at a dose of 10 mg/kg×3 (s.c.) significantly reduced the swelling with respect to the vehicle control. This effect was similar to Indomethacin (30 mg/kg×3). These results show that a histamine $H_4$ receptor antagonist can act as an anti-inflammatory agent.

Example 5
Cell-type Distribution of $H_4$ Expression

RNA was prepared from the different cells using a RNeasy kit (Qiagen, Valencia, Calif.) according to the manufacturer's instructions. RNA samples (5 μg) were run on an RNA gel and then transferred overnight to a nylon blot (Hybond, Amersham Pharmacia Biotech, Piscataway, N.J.). The blot was pre-hybridized with ExpressHyb solution (CLONTECH) for 30 min at 68° C. The $H_4$ receptor DNA was labeled using the rediprime II kit (Amersham Pharmacia Biotech). The blot was hybridized for 2 h at 68° C., followed by one wash step (23 SSC and 0.05% SDS) of 40 min at room temperature, and a second wash step (0.13 SSC and 0.1% SDS) of 40 min at 50° C. The blot was exposed to X-ray film at 27° C. with two intensifying screens overnight.

Conclusion

The Northern Blot results indicate that the $H_4$ receptor is expressed on bone-marrow derived mast cells (BMMC) peritoneal mast cells, and eosinophils. These positive results are consistent with the published literature (eg. Oda et al., Nguyen et al., and Morse et al. in the Background section). However, the negative results of the Northern Blot experiment, such as the finding of apparently no measurable levels of $H_4$ receptor expressed by neutrophils, differ somewhat from the above literature findings. This may be explained by the different methodologies used. Additional investigation may also clarify these issues.

TABLE 4

Cell-type Distribution of $H_4$ Expression by Northern Blot

| Species | Cell Type | $H_4$ |
|---|---|---|
| Human | Eosinophils | + |
| | Immature Dendritic Cells | − |
| | Mature Dendritic Cells | − |

TABLE 4-continued

Cell-type Distribution of $H_4$ Expression by Northern Blot

| Species | Cell Type | $H_4$ |
|---|---|---|
| | $CD14^+$ Monocytes | − |
| | $CD4^+$ T Cells | − |
| | $CD8^+$ T Cells | − |
| | B Cells | − |
| | Neutrophils | − |
| Mouse | Eosinophils | + |
| | Peritoneal Mast Cells | + |
| | BMMC | + |
| | BM Derived Macrophages | − |
| | Peritoneal Macrophages | − |
| | $CD4^+$ T Cells | − |
| | B Cells | − |

G. Other Embodiments

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. These other embodiments are also within the scope of the invention.

What is claimed is:

1. A compound of formula (I) wherein:

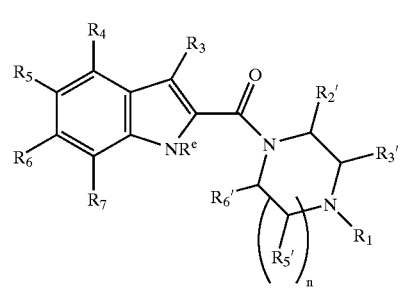

(I)

Wherein $R_1$ is $R_a$, $R_aR_b$—, $R_a$—O—$R_b$—, or $(R_c)(R_d)$N—$R_b$—, where $R_a$ is H, cyano, —(C=O)N($R_c$)($R_d$), —C(=NH)(NH$_2$), $C_{1-10}$ alkyl, $C_{3-8}$ alkenyl, $C_{3-8}$ cycloalkyl, $C_{2-5}$ heterocyclic radical, or phenyl; where $R_b$ is $C_{1-8}$ alkylene, $C_{2-8}$ alkenylene, $C_{3-8}$ cycloalkylene, bivalent $C_{3-8}$ heterocyclic radical, or phenylene; and $R_c$ and $R_d$ are each independently H, $C_{1-8}$ alkyl, $C_{2-8}$ alkenyl, $C_{3-8}$ cycloalkyl, or phenyl;

$R_2'$ is H, methyl, ethyl, $NR_pR_q$, —(CO)$NR_pR_q$, —(CO)$OR_r$, —CH$_2NR_pR_q$, or $CH_2OR_r$; where $R_p$, $R_q$, and $R_r$ are independently selected from $C_{1-6}$ alkyl, $C_{3-6}$ cycloalkyl, phenyl; ($C_{3-6}$ cycloalkyl)($C_{1-2}$ alkylene), benzyl or phenethyl; or $R_p$ and $R_q$ taken together with the nitrogen to which they are attached, form a 4–7 membered heterocyclic ring with 0 or 1 additional heteroatoms selected from O, S, and N;

$R_3'$ is H, methyl, ethyl, $NR_sR_t$, —(CO)$NR_sR_t$, —(CO)$OR_u$, —CH$_2NR_sR_t$, or $CH_2OR_u$; where $R_s$, $R_t$, and $R_u$ are independently selected from $C_{1-6}$ alkyl, $C_{3-6}$ cycloalkyl, phenyl; ($C_{3-6}$ cycloalkyl)($C_{1-2}$ uualkylene), benzyl or phenethyl; or $R_s$ and $R_t$ taken together with the nitrogen to which they are attached, form a 4–7 membered heterocyclic ring with 0 or 1 additional heteroatoms selected from O, S, and N;

$R_5'$ is methyl, ethyl, or H;

$R_6'$ is methyl, ethyl, or H;

$R_7'$ is methyl, ethyl, or H;

$R_3$ is F, Cl, Br, CHO, $R_f$, $R_f R_g$—, $R_f$—O—$R_g$—, or $(R_h)(R_i)$N—$R_g$—, where $R_f$ is H, $C_{1-6}$alkyl, $C_{2-6}$alkenyl, $C_{3-6}$cycloalkyl, $C_{2-5}$heterocyclic radical, or phenyl; where $R_g$ is $C_{1-6}$alkylene, $C_{2-6}$alkenylene, $C_{3-6}$cycloalkylene, bivalent $C_{3-6}$heterocyclic radical, or phenylene; and $R_h$ and $R_i$ are each independently H, $C_{1-6}$alkyl, $C_{2-6}$alkenyl, $C_{3-6}$cycloalkyl, or phenyl;

$R_e$ is H or $C_{1-6}$ alkyl;

each of $R_4$ and $R_6$ is independently H, F, Cl, Br, I, COOH, OH, nitro, amino, cyano, $C_{1-4}$alkoxy, or $C_{1-4}$alkyl;

$R_5$ is H, F, Cl, Br, I, (C=O)$R_j$, OH, nitro, N$R_jR_k$, cyano, phenyl, —OCH$_2$—Ph, $C_{1-4}$alkoxy, or $C_{1-4}$alkyl;

$R_7$ is H, F, Cl, Br, I, (C=O)$R_m$, OH, nitro, N$R_lR_m$, cyano, phenyl, —OCH$_2$—Ph $C_{1-4}$alkoxy, or $C_{1-4}$alkyl;

wherein each of $R_j$, $R_k$, $R_l$, and $R_m$ is independently selected from H, $C_{1-6}$ alkyl, hydroxy, phenyl, benzyl, phenethyl, and $C_{1-6}$ alkoxy;

each of the above hydrocarbyl (including alkyl, alkoxy, phenyl, benzyl, cycloalkyl, and so on) or heterocyclic groups being independently and optionally substituted with between 1 and 3 substituents selected from $C_{1-3}$ alkyl, halo, hydroxy, amino, and $C_{1-3}$ alkoxy;

wherein n is 0, 1, or 2; where n is 2, the moiety —(CHR$_5'$)$_{n=2}$— is —(CHR$_5'$—CHR$_7'$)— where CHR$_5'$ is between CHR$_6'$ and CHR$_7'$;

provided at least one of $R_1$, $R_2'$, $R_3$, $R_4$, $R_5$, $R_6$, and $R_7$ is other than H;

and provided, where n=1, and each of $R_4$, $R_5$, $R_6$, $R_7$, $R_2'$, $R_3'$, $R_5'$, and $R_6'$ is H, then (a) where $R_e$ is H, then $R_1$ is not methyl, pyridyl, phenyl, or benzyl;

and provided, where $R_e$ is H, n=1, $R_1$ is methyl, and each of $R_4$, $R_6$, $R_7$, $R_2'$, $R_3'$, $R_5'$, and $R_6'$ is H, then $R_5$ is not methoxy;

or a pharmaceutically acceptable salt, ester, or amide thereof.

2. A compound of claim 1 of the following formula wherein:

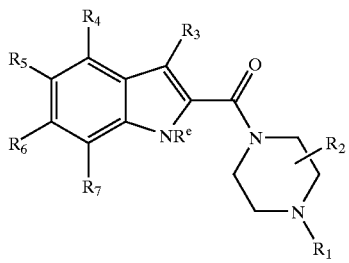

Wherein $R_1$ is $R_a$, $R_aR_b$—, $R_a$—O—$R_b$—, or $(R_c)(R_d)$N—$R_b$—, where $R_a$ is H, $C_{1-10}$ alkyl, $C_{3-8}$ alkenyl, $C_{3-8}$ cycloalkyl, $C_{2-5}$ heterocyclic radical, or phenyl; where $R_b$ is $C_{1-8}$ alkylene, $C_{3-8}$ alkenylene, $C_{3-8}$ cycloalkylene, bivalent $C_{3-8}$ heterocyclic radical, or phenylene; and $R_c$ and $R_d$ are each independently H, $C_{1-8}$ alkyl, $C_{2-8}$ alkenyl, $C_{3-8}$ cycloalkyl, or phenyl;

$R_2$ is ortho or meta, and is methyl or H;

$R_3$ is F, Cl, Br, $R_f$, $R_fR_g$—, $R_f$—O—$R_g$—, or $(R_h)(R_i)$N—$R_g$—, where $R_f$ is H, $C_{1-6}$ alkyl, $C_{2-6}$ alkenyl, $C_{3-6}$ cycloalkyl, $C_{2-5}$ heterocyclic radical, or phenyl; where $R_g$ is $C_{1-6}$ alkylene, $C_{2-6}$ alkenylene, $C_{3-6}$ cycloalkylene, bivalent $C_{3-6}$ heterocyclic radical, or phenylene; and $R_h$ and $R_j$ are each independently H, $C_{1-6}$ alkyl, $C_{2-6}$ alkenyl, $C_{3-6}$ cycloalkyl, or phenyl;

$R_e$ is H or $C_{1-6}$ alkyl;

each of $R_4$ and $R_6$ is independently H, F, Cl, Br, I, COOH, OH, nitro, amino, cyano, $C_{1-x}$alkoxy, or $C_{1-4}$ alkyl;

$R_5$ is H, F, Cl, Br, I, (C=O)$R_j$, OH, nitro, N$R_jR_k$, cyano, —OCH$_2$—Ph, $C_{1-4}$ alkoxy, or $C_{1-4}$ alkyl;

$R_7$ is H, F, Cl, Br, I, (C=O)$R_m$, OH, nitro, N$R_lR_m$, cyano, $C_{1-4}$ alkoxy, or $C_{1-4}$ alkyl;

wherein each of $R_j$, $R_k$, $R_l$, and $R_m$ is independently selected from H, $C_{1-6}$ alkyl, hydroxy, phenyl, benzyl, phenethyl, and $C_{1-6}$ alkoxy;

each of the above hydrocarbyl or heterocyclic groups being independently and optionally substituted with between 1 and 3 substituents selected from $C_{1-3}$ alkyl, halo, hydroxy, amino, and $C_{1-3}$ alkoxy;

provided at least one of $R_1$, $R_2$, $R_3$, $R_4$, $R_5$, $R_6$, and $R_7$ is other than H;

or a pharmaceutically acceptable salt, ester, or amide thereof.

3. A compound of claim 1, wherein $R_1$ is $R_a$, $R_aR_b$—, $R_a$—O—$R_b$—, or $(R_c)(R_d)$N—$R_b$—, where $R_a$ is H, $C_{1-10}$ alkyl, $C_{2-5}$ alkenyl, $C_{3-8}$ cycloalkyl, $C_{2-5}$ heterocyclic radical, or phenyl; where $R_b$ is $C_{1-6}$ alkylene, or $C_{2-8}$ alkenylene; and $R_c$ and $R_d$ are each independently H, $C_{1-8}$ alkyl, $C_{2-8}$ alkenyl, $C_{3-8}$ cycloalkyl, or phenyl;

$R_2'$ is methyl or H;

$R_3'$ is methyl or H;

$R_5'$ is methyl or H;

$R_6'$ is methyl or H;

$R_7'$ is methyl or H;

$R_3$ is F, Cl, Br, methyl, ethyl, or propyl;

$R_e$ is H or $C_{1-6}$ alkyl;

each of $R_4$ and $R_6$ is independently H, F, Cl, Br, I, COOH, OH, nitro, amino, cyano, $C_{1-3}$ alkoxy, or $C_{1-3}$ alkyl;

$R_5$ is H, F, Cl, Br, I, (C=O)$R_j$, OH, nitro, N$R_jR_k$, cyano, —OCH$_2$—Ph, $C_{1-4}$ alkoxy, or $C_{1-4}$ alkyl;

$R_7$ is H, F, Cl, Br, I, (C=O)$R_m$, OH, nitro, N$R_lR_m$, cyano, $C_{1-4}$ alkoxy, or $C_{1-4}$ alkyl;

wherein each of $R_j$, $R_k$, $R_l$, and $R_m$ is independently selected from H, $C_{1-6}$ alkyl, hydroxy, phenyl, benzyl, phenethyl, and $C_{1-6}$ alkoxy;

each of the above hydrocarbyl or heterocyclic groups being independently and optionally substituted with between 1 and 3 substituents selected from $C_{1-3}$ alkyl, halo, hydroxy, amino, and $C_{1-3}$ alkoxy;

n is 1;

provided at least one of $R_1$, $R_2'$, $R_3$, $R_4$, $R_5$, $R_6$, and $R_7$ is other than H;

or a pharmaceutically acceptable salt, ester, or amide thereof.

4. A compound of claim 1, wherein $R_1$ is H, methyl, or ethyl;

One of $R_2'$ and $R_3'$ is methyl, and the other is H, where $R_1$ is H; $R_2$ is otherwise H;

$R_e$ is H or $C_{1-3}$ alkyl;

each of $R_4$ and $R_6$ is independently H, OH, $C_{1-4}$ alkyl, $C_{1-4}$ alkoxy, cyano, or amino;

$R_5$ is H, F, Cl, Br, COOH, OH, amino, cyano, $C_{1-4}$ alkoxy, or $C_{1-4}$ alkyl; and

67

$R_7$ is H, F, Cl, Br, $C_{1-4}$ alkyl, $C_{1-4}$ alkoxy, cyano, or amino; provided at least one of $R_5$ and $R_7$ is not H.

5. A compound of claim 1, wherein $R_1$ is H, methyl, or ethyl;

$R_2'$ and $R_3'$ are independently methyl or H;

$R_3$ is H, F, or Cl;

$R_e$ is H or $C_{1-6}$ alkyl;

each of $R_4$ and $R_6$ is H;

$R_5$ is H, F, Cl, Br, methyl, ethyl, or propyl; and $R_7$ is H, F, Cl, Br, or $C_{1-4}$ alkyl; provided at least one of $R_5$ and $R_7$ is not H.

6. A compound of claim 1, wherein $R_1$ is H, methyl or ethyl.

7. A compound of claim 6, wherein $R_1$ is methyl.

8. A compound of claim 1, wherein $R_2'$ is H.

9. A compound of claim 1, wherein $R_2'$ is methyl.

10. A compound of claim 1, wherein $R_3$ is H or Cl.

11. A compound of claim 10, wherein $R_3$ is Cl.

12. A compound of claim 1, wherein $R_5$ is F, Cl, Br, or methyl and $R_7$ is F, Cl, or Br.

13. A compound of claim 1, wherein each of $R_5$ and $R_7$ is independently selected from H, F, Cl, Br, and methyl, provided at least one of $R_5$ and $R_7$ is not H.

14. A compound of claim 1, wherein each of $R_4$ and $R_6$ is independently H, methyl, or Cl.

15. A compound of claim 1, wherein $R_3$ is H or Cl; $R_5$ is F, Cl, Br, or methyl; and $R_7$ is H, F, Cl, or Br.

16. A compound of claim 15, wherein each of $R_4$ and $R_6$ is independently H, methyl, or Cl.

17. A compound of claim 1 selected from: (5-Chloro-1H-indol-2-yl)-(4-methyl-piperazin-1-yl)-methanone; (5-Fluoro-1H-indol-2-yl )-(4-methyl-piperazin-1-yl)-methanone; (5-Bromo-1H-I indol-2-yl)-(4-methyl-piperazin-1-yl)-methanone; (5-Methyl-1H-indol-2-yl)-(4-methyl-piperazin-1-yl)-methanone; (5,7-Difluoro-1H-indol-2-yl )-(4-methyl-piperazin-1-yl)-methanone; (7-Chloro-1H-indol-2-yl)-(4-methyl-piperazin-1-yl)-methanone; (5,7-Dichloro-1H-indol-2-yl)-(4-methyl-piperazin-1-yl)-methanone; and (3,5-Dichloro-1H-indol-2-yl)-(4-methyl-piperazin-1-yl )-methanone.

18. A compound of claim 1 selected from: (6-Chloro-1H-indol-2-yl)-(4-methyl-piperazinyl-1-yl)-methanone; (1H-Indol-2-yl)-(3-methyl-piperazin-1-yl )-methanone; and (7-Bromo-1H-indol-2-yl)-(4-methyl-piperazin-1-yl)-methanone.

19. A compound of claim 17 selected from: (5-Chloro-1H-indol-2-yl)-(4-methyl-piperazin-1-yl)-methanone; (5-Bromo-1H-indol-2-yl )-(4-methyl-piperazin-1-yl )-methanone; (5-Methyl-1H-indol-2-yl )-(4-methyl-piperazin-1-yl )-methanone; (5,7-Difluoro-1H-indol-2-yl)-(4-methyl-piperazin-1-yl)-methanone; and (5,7-Dichloro-1H-indol-2-yl)-(4-methyl-piperazin-1-yl)-methanone.

20. A compound of claim 1, selected from:

(4-Methyl-piperazin-1-yl )-(5-trifluoromethyl-1H-indol-2-yl )-methanone; (7-Amino-5-methyl-1H-indol-2-yl)-(4-methyl-piperazin-1-yl)-methanone; (5-Amino-7-methyl-1H-indol-2-yl)-(4-methyl-piperazin-1-yl)-methanone; (7-Amino-5-bromo-1H-indol-2-yl)-(4-methyl-piperazin-1-yl)-methanone; (5-Amino-7-bromo-1H-indol-2-yl)-(4-methyl-piperazin-1-yl)-methanone; (5-Fluoro-7-methyl-1H-indol-2-yl)-(4-methyl-piperazin-1-yl)-methanone; (7-Fluoro-5-methyl-1H-indol-2-yl)-(4-methyl-piperazin-1-yl)-methanone; (6-Bromo-5-hydroxy-1H-indol-2-yl)-(4-methyl-piperazin-1-yl)-methanone; (5-Bromo-6-hydroxy-1H-indol-2-yl)-(4-methyl-piperazin-1-yl)-

68 methanone; (6-Bromo-7-hydroxy-1H-indol-2-yl)-(4-methyl-piperazin-1-yl)-methanone; (4-Bromo-7-hydroxy-1H-indol-2-yl)-(4-methyl-piperazin-1-yl)-methanone; (6-Bromo-7-methyl-1H-indol-2-yl)-(4-methyl-piperazin-1-yl)-methanone; and (4-Bromo-7-methyl-1H-indol-2-yl)-(4-methyl-piperazin-I-yl)-methanone.

21. A compound of claim 1, selected from: (5,7-Dichloro-1H-indol-2-yl)-piperazin-1-yl-methanone; (5,7-Difluoro-1H-indol-2-yl)-piperazin-1-yl-methanone; (5, 7-Difluoro-1H-indol-2-yl)-(3-methyl-piperazin-1-yl)-methanone; (5,6-Difluoro-1H-indol-2-yl)-(4-methyl-piperazin-1-yl)-methanone; and (4,6-Difluoro-1H-indol-2-yl)-(4-methyl-piperazin-1-yl)-methanone.

22. A compound of claim 1, selected from:

1-(5-Chloro-1H-indole-2-carbonyl)-4-methyl-piperazine-2-carboxylic acid methyl ester; 4-(5-Chloro-1H-indole-2-carbonyl)-1-methyl-piperazine-2-carboxylic acid methyl ester; 4-(5-Chloro-1H-indole-2-carbonyl)-1-methyl-piperazine-2-carboxylic acid amide; 1-(5-Chloro-1H-indole-2-carbonyl)-4-methyl-piperazine-2-carboxylic acid amide; 4-(5-Chloro-1H-indole-2-carbonyl)-1-methyl-piperazine-2-carboxylic acid methylamine; 1-(5-Chloro-1H-indole-2-carbonyl)-4-methyl-piperazine-2-carboxylic acid methylamide; 4-(5-Chloro-1H-indole-2-carbonyl)-1-methyl-piperazine-2-carboxylic acid dimethylamide; 1-(5-Chloro-1H-1-indole-2-carbonyl)-4-methyl-piperazine-2-carboxylic acid dimethylamide; (5-Chloro-1H-indol-2-yl)-(3-hydroxymethyl-4-methyl-piperazin-1-yl)-methanone; (5-Chloro-1H-indol-2-yl)-(3-methoxymethyl-4-methyl-piperazin-1-yl )-methanone; (5-Chloro-1H-indol-2-yl)-(2-methoxymethyl-4-methyl-piperazin-1-yl)-methanone; (5-Chloro-1H-indol-2-yl)-(4-methyl-3-methylaminomethyl-piperazin-1-yl)-methanone; (5-Chloro-1H-indol-2-yl)-(4-methyl-2-methylaminomethyl-piperazin-1-yl)-methanone; (5-Chloro-1H-indol-2-yl)-(3-dimethylaminomethyl-4-methyl-piperazin-1-yl)-methanone; and (5-Chloro-1H-indol-2-yl)-(2-dimethylaminomethyl-4-methyl-piperazin-1-yl)-methanone.

23. A pharmaceutical composition comprising a compound of claim 1 and a pharmaceutically acceptable carrier.

24. A pharmaceutical composition comprising a compound of claim 2 and a pharmaceutically acceptable carrier.

25. A pharmaceutical composition comprising a compound of claim 3 and a pharmaceutically acceptable carrier.

26. A pharmaceutical composition of claim 20, comprising a compound selected from (5-Chloro-1H-indol-2-yl)-(4-methyl-piperazin-1-yl)-methanone; (5-Fluoro-1H-indol-2-yl)-(4-methyl-piperazin-1-yl)-methanone; (5-Bromo-1H-indol-2-yl)-(4-methyl-piperazin-1-yl)-methanone; (5-Methyl-1H-indol-2-yl)-(4-methyl-piperazin-1-yl)-methanone; (5,7-Difluoro-1H-indol-2-yl)-(4-methyl-piperazin-1-yl)-methanone; (7-Chloro-1H-indol-2-yl)-(4-methyl-piperazin-1-yl)-methanone; (5,7- Dichloro-1H-indol-2-yl)-(4-methyl-piperazin-1-yl)-methanone; (3,5-Dichloro-1H-indol-2-yl)-(4-methyl-piperazin-1-yl)-methanone; (6-Chloro-1H-indol-2-yl)-(4-methyl-piperazin-1-yl)-methanone; (1H-Indol-2-yl)-(3-methyl-piperazin-1-yl)-methanone; and (7-Bromo-1H-indol-2-yl)-(4-methyl-piperazin-1-yl)-methanone.

27. A packaged drug comprising (a) a pharmaceutical composition comprising a compound of claim 1, 2, or 3 and a pharmaceutically acceptable carrier, and (b) instructions for the administration of said composition for the treatment or prevention of an $H_4$-mediated disease or condition.

28. A method for treating an $H_4$-mediated condition in a patient, said method comprising administering to the patient a pharmaceutically effective amount of a composition comprising a compound of claim 1.

29. A method for treating an $H_4$-mediated condition in a patient, said method comprising administering to the patient a pharmaceutically effective $H_4$-inhibiting amount of a composition comprising a compound of claim 1.

30. A method of claim 29 wherein said compound is a compound of claim 2.

31. A method of claim 29, wherein said compound is a compound of claim 3.

32. A method of claim 29, wherein said compound is selected from: (5-Chloro-1H-indol-2-yl)-(4-methyl-piperazin-1-yl)-methanone; (5-Fluoro-1H-indol-2-yl)-(4-methyl-piperazin-1-yl)-methanone; (5-Bromo-1H-indol-2-yl)-(4-methyl-piperazin-1-yl)-methanone; (5-Methyl-1H-indol-2-yl)-(4-methyl-piperazin-1-yl)-methanone; (5,7-Difluoro-1H-indol-2-yl)-(4-methyl-piperazin-1-yl)-methanone; (7-Chloro-1H-indol-2-yl)-(4-methyl-piperazin-1-yl)-methanone; (5,7-Dichloro-1H-indol-2-yl)-(4-methyl-piperazin-1-yl)-methanone; (3,5-Dichloro-1H-indol-2-yl)-(4-methyl-piperazin-1-yl)-methanone; (6-Chloro-1H-indol-2-yl)-(4-methyl-piperazin-1-yl)-methanone; (1H-Indol-2-yl)-(3-methyl-piperazin-1-yl)-methanone; and (7-Bromo-1H-indol-2-yl)-(4-methyl-piperazin-1-yl)-methanone.

33. A method of claim 29, wherein said $H_4$-mediated condition is selected from: inflammatory disorders, asthma, psoriasis, rheumatoid arthritis, ulcerative colitis, Crohn's disease, inflammatory bowel disease, multiple sclerosis, allergic disorders, autoimmune disease, lymphatic disorders, and immunodeficiency disorders.

34. A method of claim 33, wherein said $H_4$-mediated condition is an inflammatory disorder or an allergic disorder.

35. A method of claim 34, wherein said inflammatory disorder is an inflammation-mediated condition selected from: acute inflammation, allergic inflammation, and chronic inflammation.

36. A method for treating asthma in a patient, said method comprising administering to the patient a pharmaceutically effective amount of a composition comprising a compound of claim 1, 18, or 19.

37. A method for treating an allergic disorder in a patient, said method comprising administering to the patient a pharmaceutically effective amount of a composition comprising a compound of claim 1, 18, or 19.

* * * * *

UNITED STATES PATENT AND TRADEMARK OFFICE
CERTIFICATE OF CORRECTION

PATENT NO. : 6,803,362 B2  Page 1 of 1
APPLICATION NO. : 10/094357
DATED : October 12, 2004
INVENTOR(S) : Nicholas I. Carruthers et al.

It is certified that error appears in the above-identified patent and that said Letters Patent is hereby corrected as shown below:

Claim 1, in column 64:
 line 28, that portion of the text reading "formula (I) wherein:" should be changed to --formula (I):--;
 line 43, that portion of the text reading "Wherein" should be changed to --wherein--;
 line 63, that portion of the text reading "($C_{1-2}$ uualkylene)" should be changed to --($C_{1-2}$ alkylene)--.

Claim 1, in column 65, line 34, that portion of the text reading "$R_5$', and $R_6$' is H, then (a) where $R_e$ is H, then $R_1$ is not" should be changed to --$R_5$', and $R_6$' is H, then $R_1$ is not--.

Claim 2, in column 66, line 6, that portion of the text reading "cyano, $C_1$- alkoxy" should be changed to --cyano, $C_{1-4}$ alkoxy--.

Claim 4, in column 66, line 60, that portion of the text reading "One of" should be changed to --one of--.

Signed and Sealed this

Seventh Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 6,803,362 B2  Page 1 of 1
APPLICATION NO. : 10/094357
DATED : October 12, 2004
INVENTOR(S) : Nicholas I. Carruthers et al.

It is certified that error appears in the above-identified patent and that said Letters Patent is hereby corrected as shown below:

Claim 26, in column 68, line 48, that portion of the text reading "A pharmaceutical composition of claim 20, comprising" should be changed to --A pharmaceutical composition of claim 23, comprising--.

Signed and Sealed this
Fifteenth Day of May, 2012

David J. Kappos
*Director of the United States Patent and Trademark Office*